US008865746B2

(12) United States Patent
Vath

(10) Patent No.: US 8,865,746 B2
(45) Date of Patent: Oct. 21, 2014

(54) METHODS OF TREATING AN OVERWEIGHT OR OBESE SUBJECT

(75) Inventor: James Vath, Lynnfield, MA (US)

(73) Assignee: Zafgen, Inc., Cambridge, MA (US)

( * ) Notice: Subject to any disclaimer, the term of this patent is extended or adjusted under 35 U.S.C. 154(b) by 98 days.

(21) Appl. No.: 12/504,722

(22) Filed: Jul. 17, 2009

(65) Prior Publication Data

US 2010/0016425 A1    Jan. 21, 2010

Related U.S. Application Data

(60) Provisional application No. 61/082,062, filed on Jul. 18, 2008, provisional application No. 61/114,673, filed on Nov. 14, 2008.

(51) Int. Cl.
*A61K 31/336* (2006.01)

(52) U.S. Cl.
CPC .................................. *A61K 31/336* (2013.01)
USPC ......................................................... 514/336

(58) Field of Classification Search
None
See application file for complete search history.

(56) References Cited

U.S. PATENT DOCUMENTS

| | | | |
|---|---|---|---|
| 5,164,410 A | 11/1992 | Kishimoto et al. | |
| 5,166,172 A | 11/1992 | Kishimoto et al. | |
| 5,180,735 A | 1/1993 | Kishimoto et al. | |
| 5,180,738 A | 1/1993 | Kishimoto et al. | |
| 5,196,406 A | 3/1993 | Kamei et al. | |
| 5,204,345 A | 4/1993 | Kishimoto et al. | |
| 5,288,722 A | 2/1994 | Kishimoto et al. | |
| 5,290,807 A | 3/1994 | Folkman et al. | |
| 5,422,363 A | 6/1995 | Yanai et al. | |
| 5,536,623 A | 7/1996 | Ohmachi et al. | |
| 5,698,586 A | 12/1997 | Kishimoto et al. | |
| 5,767,293 A | 6/1998 | Oku et al. | |
| 5,846,562 A * | 12/1998 | Yanai et al. | 424/451 |
| 5,900,431 A * | 5/1999 | Molina et al. | 514/475 |
| 6,017,949 A | 1/2000 | D'Amato et al. | |
| 6,017,954 A | 1/2000 | Folkman et al. | |
| 6,040,337 A | 3/2000 | Hong, II et al. | |
| 6,063,812 A | 5/2000 | Hong et al. | |
| 6,180,626 B1 | 1/2001 | Shimomura et al. | |
| 6,207,704 B1 | 3/2001 | Liu et al. | |
| 6,306,819 B1 | 10/2001 | Rupnick et al. | |
| 6,323,228 B1 | 11/2001 | BaMaung et al. | |
| 6,383,471 B1 | 5/2002 | Chen et al. | |
| 6,548,477 B1 | 4/2003 | Olson et al. | |
| 6,566,541 B2 | 5/2003 | Liu et al. | |
| 6,664,244 B1 * | 12/2003 | Furuse et al. | 514/58 |
| 6,803,382 B2 | 10/2004 | Eustache et al. | |
| 7,084,108 B2 | 8/2006 | Olson et al. | |
| 7,268,111 B2 | 9/2007 | Olson et al. | |
| 7,718,695 B2 | 5/2010 | Kim et al. | |
| 2004/0067266 A1 * | 4/2004 | Toppo | 424/730 |
| 2004/0204472 A1 | 10/2004 | Briggs et al. | |
| 2005/0037994 A1 * | 2/2005 | Kim et al. | 514/58 |
| 2005/0239878 A1 | 10/2005 | Thompson et al. | |
| 2006/0045865 A1 | 3/2006 | Jacob et al. | |
| 2006/0276512 A1 * | 12/2006 | Han et al. | 514/336 |
| 2007/0078172 A1 | 4/2007 | McElroy et al. | |
| 2008/0200402 A1 | 8/2008 | Alvinerie et al. | |
| 2009/0148396 A1 | 6/2009 | Akullian et al. | |
| 2010/0016425 A1 | 1/2010 | Vath | |
| 2012/0034233 A1 | 2/2012 | Hughes et al. | |

FOREIGN PATENT DOCUMENTS

| | | |
|---|---|---|
| EP | 0682020 A1 | 11/1995 |
| WO | WO-00/64876 A1 | 11/2000 |
| WO | WO-03/027104 A1 | 4/2003 |
| WO | WO-2004/033419 A1 | 4/2004 |
| WO | WO-2005/082349 A1 | 9/2005 |
| WO | WO-2006/080591 A1 | 8/2006 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |

OTHER PUBLICATIONS

"Total synthesis and antiangiogenic activity of cyclopentane analogues of fumagillol" by Jeong et al., Bioorg. Med. Chem. Lett. 15, 3580-83 (2005).*
"Obesity" in Harrison's Principles of Internal Medicine, 15$^{th}$ Ed., by Braunwald et al. (Eds.), McGraw-Hill (New York), pp. 479-486 (2001).*
Brakenhielm, E., et al., (2004) "Angiogenesis Inhibitor, TNP-470, Prevents Diet-Induced and Genetic Obesity in Mice," Circulation Research, http://circres.ahajournals.org (accessed on Feb. 8, 2007).
Dumas, J., et al., "Synthesis and Structure Activity Relationships of Novel Small Molecule Cathepsin D Inhibitors," Bioorganic & Medicinal Chemistry Letters 9 (1999) 2531-2536.
Eder, JP, et al., (2006) "Phase 1 Dose Escalation Safety & Tolerance Study of PPI-2458 in Subjects with Non-Hodgkin's Lymphoma or Solid Tumors," (Presented on Nov. 7-10, 2006 at EORTC-NCI-AACR Symposium on "Molecular Targets and Cancer Therapeutics.").
Kim, YM, et al. (2007) "Assessment of the Anti-Obesity Effects of the TNP-470 Analog, CKD-732," Journal of Molecular Endocrinology 38, 455-465.
Rupnick, MA (2002) "Adipose Tissue Mass Can be Regulated Through the Vasculature," PNA 99, 10730-10735.
Shin, SJ (2010) "A Phase I Pharmacokinetic and Pharmacodynamic Stdy of CKD-732, an Antiangiogenic Agent, in Patients with Refractory Solid Cancer," Invest New Drugs 28:650-658.
Search Report completed on Mar. 2, 2011, for International Application PCT/US2010/052050.
European Search Report for EP 09798793 dated Oct. 11, 2011, 9 pages.
Winter et al. (2006) "Endothelial αvβ3 Integrin-Targeted Fumagillin Nanoparticles Inhibit Angiogenesis in Atherosclerosis," *Arterioscler Thromb Vasc Biol.*: 2103-2109.

(Continued)

*Primary Examiner* — Wu-Cheng Winston Shen
*Assistant Examiner* — Theodore R West
(74) *Attorney, Agent, or Firm* — Goodwin Procter LLP

(57) ABSTRACT

The invention herein generally relates to pharmaceutical formulations and methods of treating an overweight or obese subject, and overweight- or obesity-related conditions.

9 Claims, 15 Drawing Sheets

(56) References Cited

OTHER PUBLICATIONS

Bernier et al. (2005) "Fumagillin class inhibitors of methionine aminopeptidase-2," *Drugs of the Future* 30(5): 497-500.
Molina et al. (2002) "Fumagillin Treatment of Intestinal Microsporidiosis," *N. Engl. J. Med.* 346(25): 1963-1969.
Picoul et al. (2003) "Progress in fumagillin synthesis," *Pure Appl. Chem.* 75(2-3): 235-249.
Seneca et al. (1956) "Amebiasis: a review. II. Laboratory diagnosis, differential diagnosis and therapy," *Am J. Digestive Dis.* 1: 310-322.
Ingber et al. (1990) "Synthetic analogues of fumagillin that inhibit angiogenesis and suppress tumour growth," *Nature* 348: 555-557.
Everhart (1993) "Contributions of Obesity and Weight Loss to Gallstone Disease," *Ann Intern Med.* 119:1029-1035.
Weinsier et al. (1993) "Gallstone Formation and Weight Loss," *Obesity Research* 1(1):51-56.
National Task Force on the Prevention and Treatment of Obesity (1993) "Very Low-Calorie Diets," *JAMA* 270(8):967-974.
Weinsier, et al. (1995) "Medically Safe Rate of Weight Loss for the Treatment of Obesity: A Guideline Based on Risk of Gallstone Formation," *The American Journal of Medicine* 98:115-117.
Pagliarulo et al. (2003) "Gallstone disease and related risk factors in a large cohort of diabetic patients," *Digestive and Liver Disease* 36:130-134.
Noel et al. (2009) "Increased Risk of Acute Pancreatitis and Biliary Disease Observed in Patients with Type 2 Diabetes," *Diabetes Care* 32(5):834-838.
Anderson, Hamilton H., "The Use of Fumagillin in Amoebiasis," *Annals New York Academy of Sciences*, 1118-1124.
Benny, Ofra, et al., (2008) "An Orally Delivered Small-Molecule Formulation with Antiangiogenic and Anticancer Activity," *Nature Biotechnology*, 26, 7:799-807.
Didier, Peter J., et al. (2006) "Antimicrosporidial Activities of Fumagillin, TNP-470, Ovalicin, and Ovalicin Derivatives in Vitro and In Vivo," Antimicrobial Agents and Chemotherapy, p. 2146-2155.
DiPaolo, J.A., et al. (1958-1959) "Studies on the Carcinolytic Activity of Fumagillin and Some of its Derivatives," *Antibiotics Annual*, 541-546.
Drevs, Joachim, et al. (2003) "Antiangiogenic Potency of FK866/K22.175, a New Inhibitor of Intracellular NAD Biosynthesis, In Murine Renal Cell Carcinoma," Anticancer Research 23: 4853-4858.
Kruger, Erwin, A., (2000) "TNP-470: An Angiogenesis Inhibitor in Clinical Development for Cancer," Exp. Opin. Invest. Drugs 9(6), pp. 1383-1396.
Lijnen, H.R., et al. (2010) "Fumagillin Reduces Adipose Tissue Formation in Murine Models of Nutritionally Induced Obesity," Obesity 18: 2241-2246.
Masiero, Laura, et al. (1997) "New Anti-angiogenesis Agents: Review of the Clinical Experience with Carboxyamido-Triazole (CAI), Thalidomide, TNP-470 and Interleukin-12," Angiogenesis, 1: 23-35.
McGowan, Max C., et al., (1951) Fumagillin (H-3), a New Antibiotic with Amebicidal Properties, Science, vol. 113, p. 202-203.
Milkowski, Deborah M., et al., *Antiangiogenic Agents in Cancer Therapy*, Chapter 22 "TNP-470," pp. 385-398.
Molina et al. (1997) "Potential Efficacy of Fumagillin in Intestinal Microsporidiosis Due to *Enterocytozoon bieneusi* in Patients with HIV Infection: Results of a Drug Screening Study," *AIDS*, 11:1603-1610.
Molina, et al. (2000) "Trial of Oral Fumagillin for the Treatment of Intestinal Microsporidiosis in Patients with HIV Infection," *AIDS*, 14:1341-1348.
Naganuma, Yasuko, et al. (2011) "Metronomic Doxifluridine Chemotherapy Combined with the Anti-Angiogenic Agent TNP=470 Inhibits the Growth of Human Uterine Carcinosarcoma Xenografts," Cancer Sci 102(8): pp. 1545-1552.
Yanai, Shigeo, et al., (1994) "Antitumor Activity of a Medium-Chain Triglyceride Solution of the Angiogenesis Inhibitor TNP-470 (AGM-1470) when Administered Via the Hepatic Artery to Rats Bearing Walker 256 Carcinosarcoma in the Liver," The Journal of Pharmacology and Experimental Therapeutics 271(3): pp. 1267-1273.

* cited by examiner

METHODS OF TREATING AN OVERWEIGHT OR OBESE SUBJECT

RELATED APPLICATIONS

This application claims the benefit of and priority to U.S. provisional application Ser. No. 61/114,673 filed Nov. 14, 2008 and 61/082,062 filed Jul. 18, 2008 in the U.S. Patent and Trademark office, the contents of each of which is hereby incorporated by reference herein in its entirety.

FIELD OF THE INVENTION

The invention generally relates to pharmaceutical formulations and methods of treating an overweight or obese subject, and treating overweight- or obesity-related conditions.

BACKGROUND OF THE INVENTION

Over 1.1 billion people worldwide are reported to be overweight. Obesity is estimated to affect over 100 million people in the United States alone. Thirty-four percent of the population in the United States over the age of twenty is considered clinically obese. While being overweight or obese presents problems (for example restriction of mobility, discomfort in tight spaces such as theater or airplane seats, social difficulties, etc.), these conditions, in particular clinical obesity, affect other aspects of health, i.e., diseases and other adverse health conditions associated with, exacerbated by, or precipitated by being overweight or obese. The estimated mortality from obesity-related conditions in the United States is over 300,000 annually (O'Brien et al. Amer J Surgery (2002) 184:4S-8S; and Hill et al. (1998) Science, 280:1371).

There is no curative treatment for being overweight or obese. Traditional pharmacotherapies for treating an overweight or obese subject, such as serotonin and noradrenergic re-uptake inhibitor, noradrenergic re-uptake inhibitors, selective serotonin re-uptake inhibitors, intestinal lipase inhibitors, or surgeries such as stomach stapling or gastric banding, have been shown to provide short-term benefits with significant rates of relapse, and have further shown harmful side-effects to patients.

More recently, certain angiogenesis inhibitors, such as TNP-470, have been investigated for use to treat obesity (Rupnick et al., U.S. Pat. No. 6,306,819). These angiogenesis inhibitors are analogs or derivatives of fumagillin, which is a known fungal metabolite produced by *A. fumigatus*. Analogs and derivates of fumagillin have been researched and developed because of adverse side-effects associated with administration of fumagillin to subjects and because of poor bioavailability of fumagillin, i.e., fumagillin exhibits rapid metabolic degradation and erratic levels in blood.

For example, famagillin has traditionally been administered as an antiparasitic agent. Fumagillin has been administered in a dose range of 10 mg to 20 mg, three times a day (30 mg/day to 60 mg/day) to humans to treat amebiasis (Seneca, Am. J. Digestive Dis. (1956) 1:310-322). Fumagillin has also been administered at 60 mg/day to humans to treat intestinal microsporidiosis due to *Enteroctozoon bieneusi* (Molina et al. Engl J Med (2002) vol. 346 25:1963-1969). Administering fumagillin at these dosages has resulted in patients developing blood disorders, e.g., thrombocytopenia, leukopenia, and neutropenia (Molina et al. Engl J Med (2002) vol. 346 25:1963-1969 and Seneca, Am. J. Digestive Dis. (1956) 1:310-322).

Further, fumagillin has been investigated as an anti-cancer agent. A resulting side-effect of administration of fumagillin to a mouse at a dose of 33 mg/kg/day is severe weight loss, i.e., wasting (Ingbar et al. (Nature (1990) 348:555-557); see also D'Amato et al. (U.S. Pat. No. 6,017,949) and BaMaung et al. (U.S. Pat. No. 6,323,228)). Wasting is characterized by degradation and loss of adipose tissue and lean body mass (muscle tissue, bones, and organs). Substantial loss of lean body mass along with loss of excess adiposity is not a desirable consequence of any therapy, let alone a therapy for an overweight or obese subject.

There is an unmet need for methods of treating overweight or obese subjects that are safe and effective.

SUMMARY

An aspect of the invention herein provides methods for treating obesity with fumagillin, fumagillol, or fumagillin ketone, or derivatives thereof, or salts, esters or prodrugs of these, without the side effect of inducing wasting of lean body mass. Accordingly, methods of the invention take advantage of the efficacy of fumagillin, fumagillol, or fumagillin ketone, or derivatives thereof, or salts, esters or prodrugs of these, for weight reduction, but without the harmful side-effects (i.e., wasting) reported in the prior art.

In one aspect, the objects of the invention are achieved through the use of preferred dosing. It has unexpectedly been discovered that low doses of fumagillin, fumagillol, or fumagillin ketone, or derivatives thereof, or salts, esters or prodrugs of these, (as compared to the traditional dosing, for example, for reduction of neoplastic tissue) results in reduction of adipose tissue without significant reduction in muscle mass. Exemplary doses include from about 1 g/day to about 0.01 mg/day. Other exemplary doses include about 500 mg/day, about 250 mg/day, preferably equal to or less than about 100 mg/day, about 50 mg/day, more preferably equal to or less than about 25 mg/day, about 10 mg/day, about 5 mg/day, about 3 mg/day, about 2 mg/day, about 1 mg/day, about 0.75 mg/day, about 0.5 mg/day, about 0.1 mg/day, and about 0.05 mg/day. Other doses will be apparent upon consideration of the principles of the invention disclosed herein.

In another aspect, the invention generally relates to a method of treating an overweight- or obesity-related condition or co-morbidity in which an amount of fumagillin, fumagillol, or fumagillin ketone, or derivatives thereof, or salts, esters or prodrugs of these, effective to reduce or eliminate the co-morbidity, but that does not substantially alter lean body mass, is administered to a subject. Exemplary co-morbidities include a cardiac disorders, endocrine disorders, respiratory disorders, hepatic disorders, skeletal disorders, psychiatric disorders, metabolic disorders, metabolic disorders, sleeping disorders, and reproductive disorders.

Exemplary cardiac disorders include hypertension, dyslipidemia, ischemic heart disease, cardiomyopathy, cardiac infarction, stroke, venous thromboembolic disease and pulmonary hypertension. Exemplary endocrine disorders include type 2 diabetes and latent autoimmune diabetes in adults. Exemplary respiratory disorders include obesity-hypoventilation syndrome, asthma, and obstructive sleep apnea. An exemplary hepatic disorder is nonalcoholic fatty liver disease. Exemplary skeletal disorders include back pain and osteoarthritis of weight-bearing joints. Exemplary metabolic disorders include Prader-Willi Syndrome and polycystic ovary syndrome. Exemplary sleeping disorders include sleep apnea. Exemplary reproductive disorders include sexual dysfunction, erectile dysfunction, infertility, obstetric complications, and fetal abnormalities. Exemplary psychiatric disorders include weight-associated depression and anxiety.

Another aspect of the invention provides methods for treating obesity with fumagillin, fumagillol, or fumagillin ketone, or derivatives thereof, or salts, esters or prodrugs of these, without the side effect of developing a blood disorder. Accordingly, methods of the invention take advantage of the efficacy of fumagillin, fumagillol, or fumagillin ketone, or derivatives thereof, or salts, esters or prodrugs of these, for weight reduction, but without the harmful side-effects (i.e., blood disorders or wasting) reported in the prior art.

In one aspect, the objects of the invention are achieved through the use of preferred dosing. It has unexpectedly been discovered that low doses of fumagillin, fumagillol, or fumagillin ketone, or derivatives thereof, or salts, esters or prodrugs of these, (as compared to the traditional dosing, for example, for treating a parasitic infection or for reduction of neoplastic tissue) results in reduction of adipose tissue without significant side-effects, i.e., blood disorders or wasting. Exemplary doses include from about 25 mg/day to about 0.01 mg/day. Other preferred doses include about 10 mg/day, about 5 mg/day, about 3 mg/day, about 2 mg/day, about 1 mg/day, about 0.75 mg/day, about 0.5 mg/day, about 0.1 mg/day, and about 0.05 mg/day. Other doses will be apparent upon consideration of the principles of the invention disclosed herein.

In another aspect, the invention generally relates to a method of treating an overweight- or obesity-related condition or co-morbidity in which an amount of fumagillin, fumagillol, or fumagillin ketone, or derivatives thereof, or salts, esters or prodrugs of these, effective to reduce or eliminate the co-morbidity, but that does not result in development of a blood disorder in the subject. Exemplary overweight- or obesity-related conditions are described above.

In another aspect, the invention provides methods for treating an overweight or obese subject that is also afflicted with overweight- or obesity-related conditions by administering fumagillin, fumagillol, or fumagillin ketone, or derivatives thereof, or salts, esters or prodrugs of these, in combination with an agent that ameliorates, arrests, or eliminates the overweight- or obesity-related condition. Methods of the invention take advantage of the efficacy of fumagillin, fumagillol, or fumagillin ketone, or derivatives thereof, or salts, esters or prodrugs of these, for weight reduction. Further, because being overweight or obese is associated with other adverse health conditions or co-morbidities, administering fumagillin, fumagillol, or fumagillin ketone, or derivatives thereof, or salts, esters or prodrugs of these, brings a benefit in ameliorating, arresting development of or, in some cases, even eliminating, these overweight- or obesity-related conditions or co-morbidities. This benefit is increased by administering fumagillin, fumagillol, or fumagillin ketone, or derivatives thereof, or salts, esters or prodrugs of these, in combination with at least one other agent that has previously been shown to treat these overweight- or obesity-related conditions. Such conjoint treatment may be achieved by way of simultaneous, sequential or separate administration of individual components of the methods of the invention. Simultaneous administration may be in a single formulation or in separate formulations whether enteral or parenteral.

Exemplary such co-morbidities are described above. Exemplary agents to be administered in combination with fumagillin, fumagillol, or fumagillin ketone, or derivatives thereof, or salts, esters or prodrugs of these, to treat the above overweight- or obesity-related conditions or co-morbidities include: sulfonylureas; meglitinides; biguanides; thiazolidinediones; alpha-glucosidase inhibitors; dipeptidylpeptidase-4 inhibitors; sodium:glucose co-transporter inhibitors; 11 beta hydroxycorticosterone dehydrogenase 1 inhibitors; glucagon-like peptide-1 analogs or mimetics; loop diuretics; potassium-sparing agents; peripheral agents; central alpha-agonists; alpha-blockers; beta-blockers; combined alpha- and beta-blockers; direct vasodilators; calcium antagonists; dihydropyridines; ACE inhibitors; Angiotensin II receptor blockers; renin inhibitors soluble epoxide hydrolase inhibitors; statins; nitrates; inotropic agents; diuretics; anti-arrhythmic agents; thrombolytic agents; anti-platelet agents; anticoagulant agents; potassium; vasodilators; bronchodilators, anti-inflammatory agents, leukotriene blockers, and anti-Ige agents; Modafmil; antioxidants; insulin sensitizers; hepatoprotectants, lipid-lowering agents; non-steroidal anti-inflammatory agents; COX-2 inhibitors; steroids; supplements; phosphodiesterase inhibitors; prostaglandin E analogs; alkaloids; Bromocriptine, Gonadotropin-releasing Hormone (GnRH); GnRH agonist; GnRH antagonist; Tamoxifen/nolvadex; gonadotropins; Human Chorionic Gonadotropin (HCG); Human Menopausal Gonadotropin (HmG); progesterone; recombinant follicle stimulating hormone (FSH); Urofollitropin; Follitropin alfa; Follitropin beta; human growth hormone (HGH); somatropin; weight loss agents; combinations of synthetic estrogen and progesterone; Spironolactone; Eflornithine; Clomiphene; Bupivacaine hydrochloride; Dinoprostone PGE2; Meperidine HCl; Ferro-folic-500/iberet-folic-500; Meperidine; Methylergonovine maleate; Ropivacaine HCl; Nalbuphine HCl; Oxymorphone HCl; Oxytocin; Dinoprostone; Ritodrine; Scopolamine hydrobromide; Sufentanil citrate; Oxytocic; serotonin reuptake inhibitors; tricyclic antidepressants; monoamine oxidase inhibitors; psychostimulants; antipsychotics; mood stabilizers; and benzodiazepines.

In another aspect, the invention provides methods for facilitating and maintaining weight loss in a subject including administering to the subject an amount of fumagillin, fumagillol, or fumagillin ketone, or derivatives thereof, or salts, esters or prodrugs of these, effective to result in weight loss in the subject; and administering a therapeutically effective amount of a weight loss drug to maintain a reduced weight in the subject. Exemplary weight loss drugs include serotonin and noradrenergic re-uptake inhibitors; noradrenergic re-uptake inhibitors; selective serotonin re-uptake inhibitors; and intestinal lipase inhibitors. In certain embodiments, the weight loss drug is selected from the group consisting of orlistat, sibutramine, methamphetamine, ionamin, phentermine, bupropion, diethylpropion, phendimetrazine, benzphetermine, pramlintide, exenatide, liraglutide, and topamax.

Another aspect of the invention provides methods for treating an overweight or obese subject involving determining a level of at least one biomarker related to being overweight or obese in the subject; and administering an amount of fumagillin, fumagillol, or fumagillin ketone, or derivatives thereof, or salts, esters or prodrugs of these, effective to achieve a target level in the subject. The methods of the invention allow for administration of fumagillin, fumagillol, or fumagillin ketone, or derivatives thereof, or salts, esters or prodrugs of these, at an appropriate dose, to an appropriate subject, and at an appropriate time. Benefits of these methods are in their accuracy, efficacy, safety, and speed.

Exemplary biomarkers include body weight, Body Mass Index (BMI), Waist/Hip ratio (WHR), plasma adipokines, and a combination thereof. Exemplary adipokines include adipsin, adiponectin, angiotensin II, BMP-9, cathepsins, estrogen, epidermal growth factor, HB-EGF, hevin, HGF, IL-6, IL-8, leptin, LIF, lipoprotein lipase, M-CSF, metallothionein-1, NGF, osteonectin, resistin, TGFβ, TNFα, VEGF, plasminogen activator inhibitor-1 (PAI-1), and estradiol.

Another aspect of the invention generally relates to a method of providing an efficacious amount of fumagillin, fumagillol, or fumagillin ketone, or derivatives thereof, or salts, esters or prodrugs of these, to an overweight or obese subject to result in weight loss, the method including: determining a level of at least one biomarker related to being overweight or obese in the subject; administering an amount of fumagillin, fumagillol, or fumagillin ketone, or derivatives thereof, or salts, esters or prodrugs of these; monitoring the level of the biomarker; and adjusting the amount of fumagillin, fumagillol, or fumagillin ketone, or derivatives thereof, or salts, esters or prodrugs of these, administered to the subject based on the level of the biomarker.

Another aspect of the invention provides a method of treating an overweight or obese subject involving determining a body mass index (BMI) of the subject; and administering an amount of fumagillin, fumagillol, or fumagillin ketone, or derivatives thereof, or salts, esters or prodrugs of these, effective to reduce the BMI of the subject to within a more normal weight range.

Another aspect of the invention provides methods for reducing non-neoplastic tissue, thus resulting maintenance of weight or in weight loss, without the side effects associated with reducing neoplastic tissue (e.g. wasting). Accordingly, methods of the invention take advantage of the efficacy of fumagillin, fumagillol, or fumagillin ketone, or derivatives thereof, or salts, esters or prodrugs of these, for maintenance of weight or weight reduction, but without the harmful side-effects (e.g., wasting) reported in the prior art.

In one aspect, the objects of the invention are achieved through the use of preferred dosing. It has unexpectedly been discovered that low doses of fumagillin, fumagillol, or fumagillin ketone, or derivatives thereof, or salts, esters or prodrugs of these, (as compared to the traditional dosing, for example, for reduction of neoplastic tissue) result in reduction of non-neoplastic tissue, thus resulting in maintenance of weight or weight loss. Exemplary doses include from about 1 g/day to about 0.01 mg/day. Other exemplary doses include about 500 mg/day, about 250 mg/day, preferably equal to or less than about 100 mg/day, about 50 mg/day, more preferably equal to or less than about 25 mg/day, about 10 mg/day, about 5 mg/day, about 3 mg/day, about 2 mg/day, about 1 mg/day, about 0.75 mg/day, about 0.5 mg/day, about 0.1 mg/day, and about 0.05 mg/day. Other doses will be apparent upon consideration of the principles of the invention disclosed herein.

Examples of non-neoplastic tissue include adipose tissue, endometrium tissue, benign polyps, hypertrophied cardiac tissue, hypertrophied renal tissue, hypertrophied prostatic tissue, and tissue containing amyloid deposits. In certain embodiments, reducing refers to decreasing size and/or growth of non-neoplastic tissue. Substantially reducing neoplastic tissue refers to, for example, affecting about 5% of tumor size in a subject, affecting about 3% of tumor size in a subject, or affecting about 1% of tumor size in a subject.

In certain embodiments of the method, the subject has a Body Mass Index measurement selected from the group consisting of at least about 25 kg/m$^2$, at least about 30 kg/m$^2$, or at least about 40 kg/m$^2$. The subject can further be afflicted with overweight- or obesity-related conditions or co-morbidities as described above. In certain embodiments, the subject has a BMI of 35 kg/m$^2$ and one or more obesity-related conditions or co-morbidities as described above.

Further, body weight is a physiologically controlled parameter, and being overweight or obese can be viewed as a chronic disease. Accordingly, another aspect of the invention generally relates to a method of promoting and maintaining a reduced size and/or growth level of non-neoplastic tissue, the method including: administering to a subject in need thereof, a first amount of fumagillin, fuamagillol, or fumagillin ketone, or derivatives thereof, or salts, esters or prodrugs of these, effective to decrease size and/or growth of non-neoplastic tissue; and administering to the subject a second amount of fumagillin, fumagillol, or fumagillin ketone, or derivatives thereof, or salts, esters or prodrugs of these, effective to maintain the reduced size and/or reduced growth level of the non-neoplastic tissue; such that the first and second amount administered do not substantially reduce neoplastic tissue.

Another aspect of the invention provides enteral pharmaceutical formulations including fumagillin, fumagillol, or fumagillin ketone, or derivatives thereof, or salts, esters or prodrugs of these, thus taking advantage of a discovery that fumagillin, fumagillol, or fumagillin ketone, or derivatives thereof, or salts, esters or prodrugs of these, demonstrate a large absorption profile in a small intestine. Accordingly, formulations of the invention improve the bioavailability of fumagillin, fumagillol, or fumagillin ketone, or derivatives thereof, or salts, esters or prodrugs of these, to take advantage of the efficacy of the molecule for weight reduction.

As provided below, preferred amounts of fumagillin, fumagillol, or fumagillin ketone, or derivatives thereof, or salts, esters or prodrugs of these, in formulations of the invention range from about 0.001 µg to about 1 g. Specifically, fumagillin, fumagillol, or fumagillin ketone, or derivatives thereof, or salts, esters or prodrugs of these, in amounts from about 0.01 mg to about 750 mg, from about 0.05 mg to about 500 mg, from about 0.5 mg to about 250 mg, from about 1 mg to about 100 mg, from about 10 mg, to about 75 mg, or from about 20 mg to about 50 mg are useful. In particular embodiments, the daily dose is about 0.1 mg to about 1 mg, from about 0.2 mg to about 2 mg, from about 0.3 mg to about 3 mg, from about 0.4 mg to about 4 mg, or from about 0.5 to about 5 mg.

To improve the bioavailability of fumagillin, fumagillol, or fumagillin ketone, or derivatives thereof, or salts, esters or prodrugs of these, formulations of the invention further includes an enteric material. The enteric material can be a polymer that is substantially insoluble in an acidic environment of a stomach, and predominantly soluble in intestinal fluids. Exemplary enteric materials include: cellulose acetate phthalate (CAP); hydroxypropyl methylcellulose phthalate (HPMCP); polyvinyl acetate phthalate (PVAP); hydroxypropyl methylcellulose acetate succinate (HPMCAS); cellulose acetate trimellitate; hydroxypropyl methylcellulose succinate; cellulose acetate succinate; cellulose acetate hexahydrophthalate; cellulose propionate phthalate; cellulose acetate maleat; cellulose acetate butyrate; cellulose acetate propionate; copolymer of methylmethacrylic acid and methyl methacrylate; copolymer of methyl acrylate, methylmethacrylate, and methacrylic acid; copolymer of methylvinyl ether and maleic anhydride; ethyl methyacrylate-methylmethacrylate-chlorotrimethylammonium ethyl acrylate copolymer; zein; shellac; copal collophorium, Eudragit L30D55, Eudragit FS30D, Eudragit L100, Eudragit S100, Kollicoat EMM30D, Estacryl 30D, Coateric, and Aquateric, and mixtures thereof.

Formulations of the invention can also include a surfactant, to assist in uptake of fumagillin, fumagillol, or fumagillin ketone, or derivatives thereof, or salts, esters or prodrugs of these, into the intestinal mucosa. The formulations can be administered in the form of a tablet, a capsule, a troche, a powder, a granule, a suspension, and a dispersion. In certain embodiments, the formulations are in a form of a unit dosage.

Another aspect of the invention provides enteral pharmaceutical formulations including fumagillin, fumagillol, or fumagillin ketone, or derivatives thereof, or salts, esters or prodrugs of these; a material that is not soluble until a pH of at least about 5.0; and a pharmaceutically acceptable carrier or excipient thereof. Another aspect of the invention provides enteral pharmaceutical formulations including fumagillin, fumagillol, or fumagillin ketone, or derivatives thereof, or salts, esters or prodrugs of these; a material that is substantially insoluble in an acidic environment of a stomach, and predominantly soluble in intestinal fluids; and a pharmaceutically acceptable carrier or excipient thereof.

Another aspect of the invention provides enteral pharmaceutical formulations including fumagillin, fumagillol, or fumagillin ketone, or derivatives thereof, or salts, esters or prodrugs of these; a plurality of enteric materials; and a pharmaceutically acceptable carrier or excipient thereof. In a related embodiment, each enteric material is soluble at a different pH. For example, a first enteric material is soluble at a pH of about 5.5, a second enteric material is soluble at a pH of about 6.5, and a third enteric material is soluble at a pH of about 7.5.

Another aspect of the invention provides methods of treating an overweight or obese subject including administering to the subject one of the above enteral pharmaceutical formulations, thereby resulting in weight loss.

In another aspect, the invention generally relates to methods of treating an overweight- or obesity-related condition or co-morbidity by administering one of the above enteral pharmaceutical formulations effective to reduce, ameliorate, or eliminate the co-morbidity. Exemplary such co-morbidities are described above.

Another aspect of the invention provides oral cavity pharmaceutical formulations comprising fumagillin, fumagillol, or fumagillin ketone, or derivatives thereof, or salts, esters or prodrugs of these, in particular formulations for buccal and sublingual administration, that bypass gastrointestinal tract absorption and subsequent portal vein entry to the liver and first-pass metabolism. Thus the formulations of the invention improve the bioavailability of fumagillin, fumagillol, or fumagillin ketone, or derivatives thereof, or salts, esters or prodrugs of these, to take advantage of the efficacy of the molecule for weight reduction.

As provided below, preferred amounts of fumagillin, fumagillol, or fumagillin ketone, or derivatives thereof, or salts, esters or prodrugs of these, in formulations of the invention range from about 0.001 µg to about 1 g. Specifically, fumagillin, fumagillol, or fumagillin ketone, or derivatives thereof, or salts, esters or prodrugs of these, in amounts from about 0.01 mg to about 750 mg, from about 0.05 mg to about 500 mg, from about 0.5 mg to about 250 mg, from about 1 mg to about 100 mg, from about 10 mg, to about 75 mg, or from about 20 mg to about 50 mg are useful. In particular embodiments, the daily dose is about 0.1 mg to about 1 mg, from about 0.2 mg to about 2 mg, from about 0.3 mg to about 3 mg, from about 0.4 mg to about 4 mg, or from about 0.5 to about 5 mg.

The invention provides formulations that include a pharmaceutically acceptable carrier or excipient thereof that is suitable for oral cavity administration. In particular, the invention provides formulations that include a pharmaceutically-acceptable carrier or excipient for buccal administration or sublingual administration. Formulations for buccal administration or sublingual administration can be in a form of a tablet, a lozenge, a wafer, or an ointment.

In embodiments in which the formulation is in the form of a tablet, a lozenge, or a wafer, the carrier is a water soluble or water dispersible carrier material. Exemplary water soluble or water dispersible carrier materials include polysaccharides, polyvinylalcohol, polyvinylpyrrolidine, cellulose derivatives, gelatin, and mixtures thereof. In embodiments in which the formulation is in the form of an ointment, the carrier or excipient thereof includes white petrolatum, polyethylene glycol, a compatible mixture of peanut oil or purified sesame oil with beeswax, or a compatible mixture of polyethylene and liquid paraffin. Formulations of the invention can also include a surfactant, to assist in uptake of fumagillin, fumagillol, or fumagillin ketone, or derivatives thereof, or salts, esters or prodrugs of these, into the oral mucosa. In certain embodiments, the formulations are in a form of a unit dosage.

Another aspect of the invention provides methods of treating an overweight or obese subject including administering to the subject one of the above pharmaceutical formulations, thereby resulting in weight loss.

In another aspect, the invention generally relates to methods of treating an overweight- or obesity-related condition or co-morbidity by administering one of the above pharmaceutical formulations effective to reduce, ameliorate, or eliminate the co-morbidity. Exemplary co-morbidities are described above.

The foregoing and other objects, features, and advantages of the invention will become apparent from the following, more particular description of certain embodiments according to the invention and accompanying drawings.

DETAILED DESCRIPTION

Figure 1:
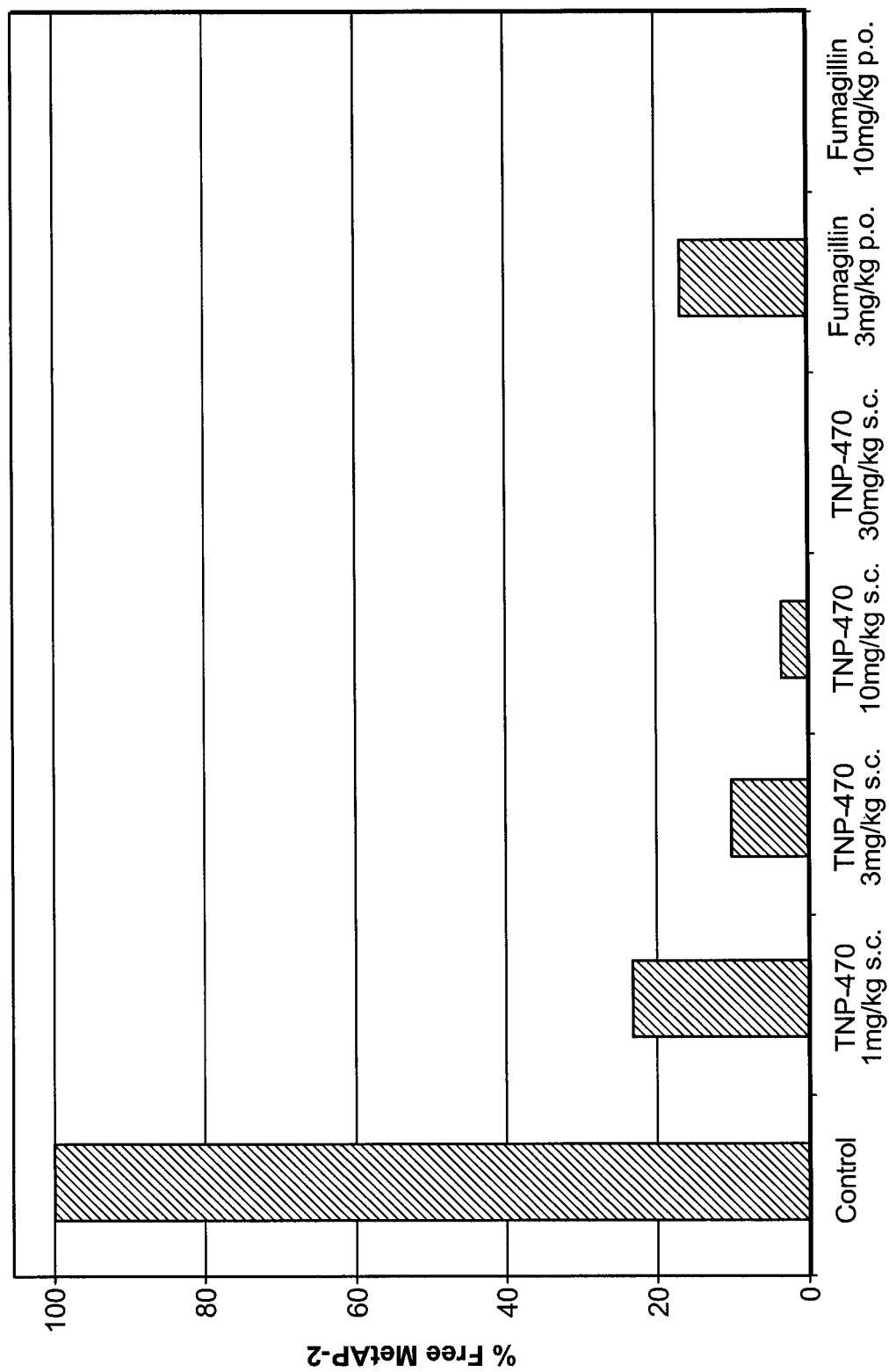
FIG. 1 is a bar graph showing binding of fumagillin and TNP-470 at different dosages to MetAP-2 in adipose tissue. Data is expressed as percent unbound (free) MetAP-2.

In certain embodiments, the invention provides methods of reducing adipose tissue in an overweight subject without substantially reducing lean body mass. A substantial reduction in lean body mass for purposes of the invention is a reduction in muscular tissue of about 8%, of about 6%, of about 4%, of about 2%, or of about 1% as compared to pretreatment levels. The subject can be a human or other mammal, such as a veterinary animal, such as a cat or a dog.

In other embodiments, The invention provides methods of reducing adipose tissue in an overweight subject without resulting in development of a blood disorder, e.g., thrombocytopenia, leukopenia, or neutropenia, in the subject.

In other embodiments, the invention provides methods of reducing non-neoplastic tissue, such as adipose tissue, endometrium tissue, benign polyps, hypertrophied cardiac tissue, hypertrophied renal tissue, hypertrophied prostatic tissue, and tissue containing amyloid deposits, thus resulting in maintenance of weight or weight loss in an overweight or obese subject, without substantially reducing neoplastic tissue.

The invention is based in part on the discovery that prevention of angiogenesis using fumagillin, fumagillol, or fumagillin ketone, or derivatives thereof, or salts, esters or prodrugs of these, reduces size or prevents growth of non-neoplastic tissue, and thus results in maintenance of weight or weight loss in a subject. Angiogenesis, also referred to as neo-vascularization, is a process by which new blood vessels are formed, and is characterized by an infiltration into the microenvironment of endothelial and smooth muscle cells. The process of angiogenesis involves proteolytic degradation of a vessel wall of a parent vessel to allow for the formation of a capillary sprout, followed by migration, proliferation, maturation of endothelial cells in a microenvironment, and recruitment of peri-endothelial cells and/or vascular smooth muscle cells to support endothelial tubes (Pathologic Basis of Disease 6th ed. Cotran, Kurnar and Collins, Saunders, Philadelphia, 1999). Persistent angiogenesis can contribute to many disease states, such as obesity.

Obesity and being overweight refer to an excess of fat in proportion to lean body mass. Excess fat accumulation is associated with increase in size (hypertrophy) as well as number (hyperplasia) of adipose tissue cells. Obesity is variously measured in terms of absolute weight, weight:height ratio, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using either of the formulas below:

| SI units | BMI = weight (kg)/height² (m²) |
| US units | BMI = weight (lb) × 703/height² (in²) |

In accordance with the U.S. Centers for Disease Control and Prevention (CDC), an overweight adult has a BMI of 25 kg/m² to 29.9 kg/m², and an obese adult has a BMI of 30 kg/m² or greater. A BMI of 40 kg/m² or greater is indicative of morbid obesity or extreme obesity. A BMI of 35 kg/m² and one or more obesity-related conditions or co-morbidities is also indicative of a subject in need of treatment. For children, the definitions of overweight and obese take into account age and gender effects on body fat.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink.

Investigations into angiogenic aspects of non-neoplastic tissue, such as adipose tissue, in overweight or obese subjects reveals a growth dependence upon the development of a vascular supply. Newly formed adipose tissue requires continued angiogenesis for further growth and development. (Wasserman (1965) The development of adipose tissue. In: Handbook of Physiology. Vol 5. Renold A., Cahill G., (eds.). Washington, D.C. Am Physiol Soc. pp. 87-100). Without being limited by any particular theory or mechanism of action, it is believed that development of adipose tissue (adipogenesis) is dependent on angiogenesis, a process of formation and development of microcirculatory units (a microcirculatory unit includes arteriols, venules, capillaries, lymphatic and interstitial tissues, and also red blood cells, leukocytes, and plasma components) that link developing tissue to the circulatory system. Thus anti-angiogeneic compounds, such as fumagillin, fumagillol, or fumagillin ketone, or derivatives thereof, or salts, esters or prodrugs of these, may be effective to reduce non-neoplastic tissue, thus resulting in weight loss in subjects.

To utilize fumagillin, fumagillol, or fumagillin ketone, or derivatives thereof, or salts, esters or prodrugs of these, as an effective therapy to reduce non-neoplastic tissue, e.g., adipose tissue, without adversely affecting a subject, the compound should be administered at dosages that do not result in side-effects, e.g., blood disorders or wasting, associated with use of fumagillin, fumagillol, or fumagillin ketone, or derivatives thereof, or salts, esters or prodrugs of these, to reduce neoplastic tissue, e.g., adipose tissue.

A blood disorder refers to a disease or disorder of the blood, e.g., thrombocytopenia, leukopenia, and neutropenia. Thrombocytopenia is a blood disorder that refers to a presence of a relatively low number of platelets, i.e., cells in blood that help blood clot. Generally, in a human, a normal platelet count ranges from about 150,000 platelets per mm$^3$ to about 450,000 platelets per mm$^3$. Symptoms of thrombocytopenia include bruising, bleeding (in particular nosebleeds or bleeding in the mouth), and rashes. Bleeding can occur with relatively minor trauma when the platelet count falls below about 50,000 platelets per mm$^3$ of blood. The most serious risk of bleeding, however, generally does not occur until the platelet count falls below 10,000 platelets per mm$^3$ to 20,000 platelets per mm$^3$. At these very low levels, bleeding may occur without any injury.

Thrombocytopenia is typically divided into three causes of low platelets: low production of platelets in the bone marrow; increased breakdown of platelets in the bloodstream (intravascular); and increased breakdown of platelets in the spleen or liver (extravascular). Disorders that involve low production in the bone marrow include aplastic anemia, cancer in the bone marrow, infections in the bone marrow, and drugs.

Leukopenia is a blood disorder that refers to a decrease in the number of circulating white blood cells (leukocytes) in the blood. A normal total white cell count is from about 4500 leukocytes per mm$^3$ to about 10,000 leukocytes per mm$^3$. A subject is diagnosed with leukopenia if their total leukocyte count drops below 4000 leukocytes per mm$^3$ in the blood. As a principal function of white cells is to combat infection, a decrease in the number of these cells, for example below 2,500 leukocytes per mm$^3$, can place subjects at increased risk for infection. Leukopenia can result from infections, such as viral infections and HIV; autoimmune disorders, such as lupus; certain medications, especially those used in chemotherapy and some antibiotics; radiation therapy; and bone marrow disease, such as leukemia or myelodysplastic syndromes.

Neutropenia is a blood disorder that refers to an abnormally low number of neutrophil granulocytes (a type of white blood cell). A normal neutrophil count is from about 1500 neutrophils per mm$^3$ to about 7000 neutrophils per mm$^3$. Three general guidelines are used to classify severity of neutropenia (based on absolute neutrophil count (ANC) measured in cells per microliter of blood): mild neutropenia, an absolute ANC count from about 1000 neutrophils per mm$^3$ to about 1500 neutrophils per mm$^3$; moderate neutropenia, an absolute ANC count from about 500 neutrophils per mm$^3$ to about 1000 neutrophils per mm$^3$; and severe neutropenia, an absolute ANC that is less than about 500 neutrophils per mm$^3$.

Neutrophils generally make up about 50% to about 70% of circulating white blood cells and serve as a primary defense against infections by destroying bacteria in the blood. A patient with neutropenia is more susceptible to bacterial infections, which may develop into neutropenic sepsis. Neutropenia is typically divided into three causes: decreased production in the bone marrow, increased destruction, and marginalization or sequestration.

Neoplastic tissue (cancer or neoplasia) is tissue that is characterized by deregulated cell growth and cell division. Cancers include carcinomas which are tumors arising in a tissue originating from endoderm or exoderm, and sarcomas which originate from mesoderm (Darnell, J., Molecular Cell Biology, Third Ed., W.H. Freeman, NY, 1990). Fumagillin has been investigated as an anti-cancer agent, however, development of fumagillin as an anti-cancer drug was discontinued due to reported adverse side-effects. For example, a resulting side-effect of administration of fumagillin to a mouse at a dose of 33 mg/kg/day to treat cancer is severe weight loss, i.e., wasting (Ingbar et al. (Nature (1990) 348:555-557; see also D'Amato et al. (U.S. Pat. No. 6,017,949) and BaMaung et al. (U.S. Pat. No. 6,323,228)).

Wasting is characterized by degradation and loss of a substantial amount of lean body mass (muscle tissue, bones, and organs) in addition to adipose tissue. In particular, lean body mass refers to structural and functional elements in cells, body water, muscle, bones, and other body organs such as the heart, liver, and kidneys. Although weight loss may involve loss of fat along with slight loss of muscle or fluid, weight loss for the purposes of maintaining health should aim to lose fat while conserving lean body mass. Wasting involves weight loss beyond normal and/or healthy levels, and in certain aspects, uncontrollable weight loss.

Treatment-induced wasting may occur as a side-effect of some drugs. High-dose sulphonamides, anti-mycobacterial agents, and other medications have been associated with anorexia and subsequent wasting. Substantial loss of lean body mass can lead to various diseases. Schaafsma (Current Topics in Nutraceutical Research (2006) ISSN 1540-7535 4(2):113-121). Health problems associated with loss of lean body mass include difficulty fighting off infection, osteoporosis, decreased muscle strength, trouble regulating body temperature, and even increased risk of death.

The invention provides dosing of the natural product, fumagillin, fumagillol, or fumagillin ketone, or derivatives thereof, or salts, esters or prodrugs of these, that result in the desirable effect of a reduction in non-neoplastic tissue, e.g., adipose tissue, but without the well-characterized side effects, e.g., development of blood disorders or loss of lean body mass. Fumagillin refers to all stereoisomers, and can be represented by the following structure:

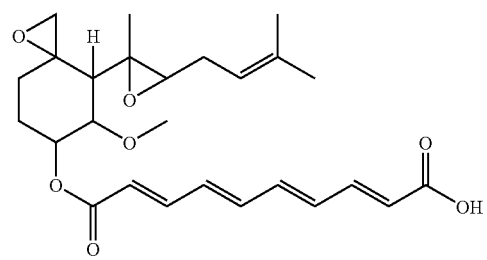 [SMILES: COC1C(OC(=O)/C=C/C=C/C=C/C=C/C(=O)O)CCC2(CO2)C1C1(C)OC1CC=C(C)C]

In certain embodiments, fumagillin has the following structure:

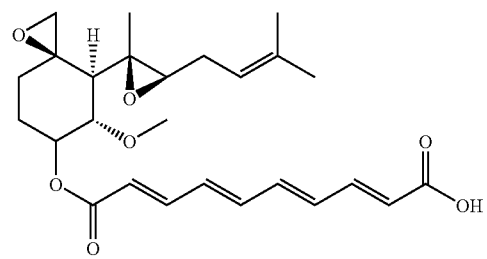 [SMILES: CO[C@@H]1C(OC(=O)/C=C/C=C/C=C/C=C/C(=O)O)CC[C@]2(CO2)[C@H]1[C@@]1(C)O[C@@H]1CC=C(C)C]

In certain other embodiments, fumagillin has the following structure:

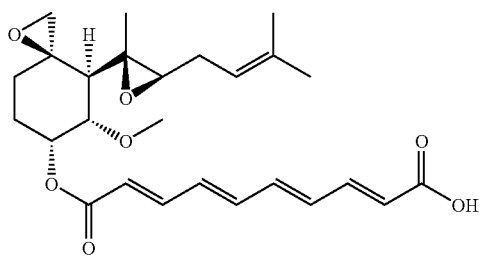 [SMILES: CO[C@@H]1[C@H](OC(=O)/C=C/C=C/C=C/C=C/C(=O)O)CC[C@]2(CO2)[C@H]1[C@@]1(C)O[C@@H]1CC=C(C)C]

Fumagillin is deposited with the Fermentation Division of the Northern Regional Research Laboratory as culture member NRIU2319. Methods of isolating fumagillin from a nutrient medium are shown in U.S. Pat. No. 2,652,356 and Hanson et al. Bacteriol. (1949) 58:527. An example of acid extraction of fumagillin is shown in U.S. Pat. No. 2,898,268. Methods of making fumagillin are shown in Picoul et al. (Pure Appl. Chem., (2003) 75:235-249). Fumagillin is also commercially available, for example, from Sigma-Aldrich (St. Louis, Mo.).

Fumagillin has a carboxylic acid moiety and can be administered in the form of the free acid. Alternatively, a salt can be prepared by reacting fumagillin free acid with a suitable base. Pharmaceutically acceptable salts illustratively include those that can be made using the following bases: ammonia, L-arginine, benethamine, benzathene, betaine, bismuth, calcium hydroxide, choline, deanol, diethanolamine, diethylarnine, 2-(diethylamino)ethanol, ethylenediamine, N-methylglucarnine, hydrabamine, 1 H-imidazole, lysine, magnesium hydroxide, 4-(2-hydroxyethyl)morpholine, piperazine, potassium hydroxide, 1-(2-hydroxyethyl)pyrrolidine, sodium hydroxide, Tris, lysine, dicyclohexylamine, triethanolamine, zinc hydroxide, diclyclohexlamine, or any other electron pair donor (as described in Handbook of Pharmaceutical Salts, Stan & Wermuth, VHCA and Wiley, Uchsenfurt-Hohestadt Germany, 2002). Esters of the present invention may be prepared by reacting fumagillin or fumagillol with the appropriate acid under standard esterification conditions described in the literature (Houben-Weyl 4th Ed. 1952, Methods of Organic Synthesis). Alternatively, esters may be formed by reacting the alcohol with an acid chlooride. Suitable fumagillin esters include ethyl methanoate, ethyl ethanoate, ethyl propanoate, propyl methanoate, propyl ethanoate, and methyl butanoate.

Fumagillol refers to all stereoisomers, and can be represented by the following structure:

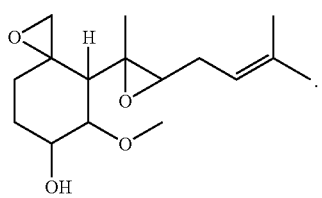 [SMILES: COC1C(O)CCC2(CO2)C1C1(C)OC1CC=C(C)C]

In certain embodiments, fumagillol has the following structure:

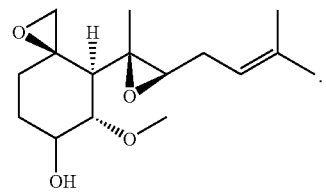 [SMILES: CO[C@@H]1C(O)CC[C@]2(CO2)[C@H]1[C@@]1(C)O[C@@H]1CC=C(C)C]

In certain embodiments, fumagillol has the following structure:

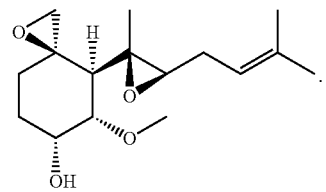 [SMILES: CO[C@@H]1[C@H](O)CC[C@]2(CO2)[C@H]1[C@@]1(C)O[C@@H]1CC=C(C)C]

Methods of making fumagillol are shown in Picoul et al. (Pure Appl. Chem., (2003) 75:235-249). Fumagillol is also commercially available, for example, from Medivet (Covington, La.).

Fumagillin ketone refers to all stereoisomers, and can be represented by the following structure:

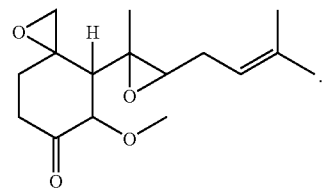 [SMILES: COC1C(=O)CCC2(CO2)C1C1(C)OC1CC=C(C)C]

In certain embodiments, fumagillin ketone has the following structure:

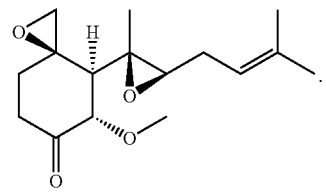 [SMILES: CO[C@@H]1C(=O)CC[C@]2(CO2)[C@H]1[C@@]1(C)O[C@@H]1CC=C(C)C]

In certain embodiments, fumagillin ketone has the following structure:

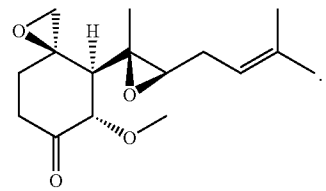 [SMILES: CO[C@@H]1C(=O)CC[C@]2(CO2)[C@H]1[C@@]1(C)O[C@@H]1CC=C(C)C]

Methods of making fumagillin ketone are shown in Picoul et al. (Pure Appl. Chem., (2003) 75:235-249). Fumagillin ketone is also commercially available, for example, from Medivet (Covington, La.).

Fumagillin, fumagillol, or fumagillin ketone, or derivatives thereof, or salts, esters or prodrugs of these, may be administered using any amount and any route of administration effective for treating an overweight or obese subject without substantially reducing lean body mass of the subject. Thus, the expression "amount effective for treating an overweight or obese subject", as used herein, refers to a sufficient amount of fumagillin, fumagillol, or fumagillin ketone, or derivatives thereof, or salts, esters or prodrugs of these, to beneficially result in weight loss without substantially reducing lean body mass of the subject.

Dosage and administration are adjusted to provide sufficient levels of fumagillin, fumagillol, or fumagillin ketone, or derivatives thereof, or salts, esters or prodrugs of these, to induce or maintain the desired effect. Additional factors that may be taken into account include the severity of the disease state, e.g., overweight, obese, or morbidly obese; age, and gender of the patient; diet, time and frequency of administration; route of administration; drug combinations; reaction sensitivities; and tolerance/response to therapy. Long acting pharmaceutical compositions might be administered hourly, twice hourly, every three to four hours, daily, twice daily, every three to four days, every week, or once every two weeks depending on half-life and clearance rate of the particular composition.

Therapeutic efficacy and toxicity of fumagillin, fumagillol, or fumagillin ketone, or derivatives thereof, or salts, esters or prodrugs of these, can be determined by standard pharmaceutical procedures. For example, therapeutic efficacy and toxicity can be determined by minimal efficacious dose or NOAEL (no observable adverse effect level). Alternatively, an ED50 (the dose is therapeutically effective in 50% of the population) and LD50 (the dose is lethal to 50% of the population) can be determined in cell cultures or experimental animals. The dose ratio of toxic to therapeutic effects is the therapeutic index, and it can be expressed as the ratio, LD50/ED50. Pharmaceutical compositions that exhibit large therapeutic indices are preferred.

Fumagillin, fumagillol, or fumagillin ketone, or derivatives thereof, or salts, esters or prodrugs of these, of the invention are preferably formulated in dosage unit form for ease of administration and uniformity of dosage. In general, the total daily usage of the compositions of the present invention will be decided by the attending physician within the scope of sound medical judgment. The therapeutically effective dose can be estimated initially either in cell culture assays or in animal models, as provided herein, usually mice, but also potentially from rats, rabbits, dogs, monkeys, or pigs. The animal model provided herein is also used to achieve a desirable concentration and total dosing range and route of administration. Such information can then be used to determine useful doses and routes for administration in humans.

For example, using a standard divisor of 12.3 for converting murine to human dosing in mg/kg as provided by the U.S. Food and Drug Administration (FDA) in its "Guidance for Industry: Estimating the Maximum Safe Starting Dose in Initial Clinical Trials for Therapeutics in Adult Healthy Volunteers" (FDA, July 2005), a murine dose of 3 mg/kg/day translates, for an overweight 80 kg adult human, to a daily dose of about 20 mg and, for an obese 100 kg adult human, to a daily dose of about 25 mg. Likewise, a murine dose of about 0.01 mg/kg/day, using the same divisor, would translate to a daily dose of about 0.06 mg to about 0.08 mg for an 80-100 kg human subject.

The daily dosage of fumagillin, fumagillol, or fumagillin ketone, or derivatives thereof, or salts, esters or prodrugs of these, may be varied over a wide range, such as about 1 g/day, 500 mg/day, about 250 mg/day, about 100 mg/day, about 50 mg/day, about 25 mg/day, about 10 mg/day, about 5 mg/day, about 3 mg/day, about 2 mg/day, about 1 mg/day, about 0.75 mg/day, about 0.5 mg/day, about 0.1 mg/day, about 0.05 mg/day, and about 0.01 mg/day.

A unit dose typically contains from about 0.001 milligrams to about 500 milligrams of the active ingredient, preferably from about 0.1 milligrams to about 100 milligrams of active ingredient, more preferably from about 1.0 milligrams to about 10 milligrams of active ingredient. An effective amount of the drug is ordinarily supplied at a dosage level of from about 0.0001 mg/kg to about 25 mg/kg of body weight per day. For example, the range is from about 0.001 to 10 mg/kg of body weight per day, or from about 0.001 mg/kg to 1 mg/kg of body weight per day.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a weight loss target, is achieved. A treatment regimen can include a corrective phase, during which a fumagillin dose sufficient to provide reduction of excess adiposity is administered, followed by a maintenance phase, during which a lower fumagillin dose sufficient to prevent re-development of excess adiposity is administered. A suitable maintenance dose is likely to be found in the lower parts of the dose ranges provided herein, but corrective and maintenance doses can readily be established for individual subjects by those of skill in the art without undue experimentation, based on the disclosure herein.

As formulated with an appropriate pharmaceutically acceptable carrier in a desired dosage, fumagillin, fumagillol, or fumagillin ketone, or derivatives thereof, or salts, esters or prodrugs of these, are administered to humans and other mammals (e.g., cats, dogs, or other vetinary animals) intravenously or topically such as ocularly, pulmonary, nasally, bucally, orally, rectally, parenterally, intracisternally, intravaginally, or intraperitoneally.

For pulmonary (e.g., intrabronchial) administration, fumagillin, fumagillol, or fumagillin ketone, or derivatives thereof, or salts, esters or prodrugs of these, can be formulated with conventional excipients to prepare an inhalable composition in the form of a fine powder or atomizable liquid.

For ocular administration, fumagillin, fumagillol, or fumagillin ketone, or derivatives thereof, or salts, esters or prodrugs of these, can be formulated with conventional excipients in the form of eye drops or an ocular implant. Among excipients useful in eye drops are viscosifying or gelling agents, to minimize loss by lacrimation through improved retention in the eye.

Liquid dosage forms for oral or other systemic administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the ocular, oral, or other systemically-delivered compositions can also include adjuvants such as wetting agents, and emulsifying and suspending agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, cutaneous routes of administration are achieved with aqueous drops, a mist, an emulsion, or a cream.

Transdermal patches have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium.

For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s). Alternatively, formulations of the invention can be administered by release from a lumen of an endoscope after the endoscope has been inserted into a rectum of a subject.

Oral dosage forms, such as capsules, tablets, pills, powders, and granules, are prepared using any suitable process known to the art. See, for example, Remington's Pharmaceutical Sciences, 18th Edition, A. Gennaro, Ed., Mack Pub. Co. (Easton, Pa. 1990), Chapters 89-91, which is hereby incorporated by reference. Typically, fumagillin, fumagillol, or fumagillin ketone, or derivatives thereof, or salts, esters or prodrugs of these, is mixed with the enteric materials and compressed into tablets. The oral dosage form can be prepared by combining an enteric material, with fumagillin, fumagillol, or fumagillin ketone, or derivatives thereof, or salts, esters or prodrugs of these, together with any other excipients for the tableting or capsule filling of beadles, using for instance a wet granulation technique or a direct compression method, to form a uniform granulate.

Alternatively, fumagillin, fumagillol, or fumagillin ketone, or derivatives thereof, or salts, esters or prodrugs of these, can be mixed with the granulate after the granulate is prepared. The moist granulated mass with or without fumagillin, fumagillol, or fumagillin ketone, or derivatives thereof, or salts, esters or prodrugs of these, is then dried and sized using a suitable screening device to provide a powder, which can then be filled into capsules or compressed into tablets or caplets, as desired.

More particularly, in a wet granulation method fumagillin, fumagillol, or fumagillin ketone, or derivatives thereof, or salts, esters or prodrugs of these, and the enteric materials and other ingredients are granulated in a granulating fluid (e.g., isopropyl alcohol, ethyl alcohol, and water) in a planetary mixer, high shear mixer, or a fluidized bed granulator. Binding agents may be contained in the granulating fluid or in the dry mix of ingredients. The wet granules are dried in an oven or a fluidized bed dryer, and then sieved through a suitable screen to obtain free flowing granules. The resulting granules may be blended with a suitable lubricant and glidant, and the lubricated granules are compressed into tablets on a rotary press using appropriate tooling.

In a direct compression method, fumagillin, fumagillol, or fumagillin ketone, or derivatives thereof, or salts, esters or prodrugs of these, the enteric materials and other ingredients are sieved through a stainless steel screen, such as a 40 mesh steel screen. The sieved materials are then charged to a suitable blender and blended for about ten minutes with an intensifier bar for about three minutes. The blend is then compressed into tablets on a rotary press using appropriate tooling.

Alternatively, formulations of the invention are incorporated into chewable tablets, crushable tablets, tablets that dissolve rapidly within the mouth, or mouth wash. Chewable tablet formulations containing enterically coated particles are known in the pharmaceutical arts (see for instance the textbook "Pharmaceutical dosage form—tablets" Vol. 1 edited by H A Lieberman et al. Marcel Dekker, Inc. (1989). Crushable tablets are conventional tablets that have the same in vitro and in vivo performance regardless of their physical integrity, i.e. tablets can be crushed and administered as a powder, e.g. on apple sauce, or mixed with water and syringed into a nasogastric or jejunostomy tube. The crushable tablets can be prepared using methods of tablet manufacturing known in the pharmaceutical art. Fast dissolving tablets containing coated particles are described, for example, in U.S. Pat. No. 6,596,311.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Additional agents include pigments, colorants, stabilizing agents, plasticizers, and glidants.

Solid compositions of a similar type may also be employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

In addition to being overweight or obese, a subject can further have an overweight- or obesity-related co-morbidities, i.e., diseases and other adverse health conditions associated with, exacerbated by, or precipitated by being overweight or obese. Because being overweight or obese is associated with other adverse health conditions or co-morbidities, administering fumagillin, fumagillol, or fumagillin ketone, or derivatives thereof, or salts, esters or prodrugs of these, brings a benefit in ameliorating, arresting development of or, in some cases, even eliminating, these overweight- or obesity-related conditions or co-morbidities. This benefit is increased by administering fumagillin, fumagillol, or fumagillin ketone, or derivatives thereof, or salts, esters or prodrugs of these, in combination with at least one other agent that has previously been shown to treat these overweight- or obesity-related conditions.

For example, type 2 diabetes has been associated with obesity. Certain complications of type 2 diabetes, e.g., disability and premature death, can be prevented, ameliorated, or eliminated by sustained weight loss (Astrup, A. Pub Health Nutr (2001) 4:499-5 15). Agents administered to treat type 2 diabetes include sulfonylureas (e.g., Chlorpropamide, Glipizide, Glyburide, Glimepiride); meglitinides (e.g., Repaglinide and Nateglinide); biguanides (e.g., Metformin); thiazolidinediones (Rosiglitazone, Troglitazone, and Pioglitazone); and alpha-glucosidase inhibitors (e.g., Acarbose and Meglitol). These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating type 2 diabetes in a subject compared to administration of one of these agents alone.

Cardiac disorders and conditions, for example hypertension, dyslipidemia, ischemic heart disease, cardiomyopathy, cardiac infarction, stroke, venous thromboembolic disease and pulmonary hypertension, have been linked to overweight or obesity. For example, hypertension has been linked to obesity because excess adipose tissue secretes substances that are acted on by the kidneys, resulting in hypertension. Additionally, with obesity there are generally higher amounts of insulin produced (because of the excess adipose tissue) and this excess insulin also elevates blood pressure. A major treatment option of hypertension is weight loss.

Agents administered to treat hypertension include Chlorthalidone; Hydrochlorothiazide; Indapamide, Metolazone; loop diuretics (e.g., Bumetanide, Ethacrynic acid, Furosemide, Lasix, Torsemide); potassium-sparing agents (e.g., Amiloride hydrochloride, Spironolactone, and Triamterene); peripheral agents (e.g., Reserpine); central alpha-agonists (e.g., Clonidine hydrochloride, Guanabenz acetate, Guanfacine hydrochloride, and Methyldopa); alpha-blockers (e.g., Doxazosin mesylate, Prazosin hydrochloride, and Terazosin hydrochloride); beta-blockers (e.g., Acebutolol, Atenolol, Betaxolol, Bisoprolol fumarate, Carteolol hydrochloride, Metoprolol tartrate, Metoprolol succinate, Nadolol, Penbutolol sulfate, Pindolol, Propranolol hydrochloride, and Timolol maleate); combined alpha- and beta-blockers (e.g., Carvedilol and Labetalol hydrochloride); direct vasodilators (e.g., Hydralazine hydrochloride and Minoxidil); calcium antagonists (e.g., Diltiazem hydrochloride and Verapamil hydrochloride); dihydropyridines (e.g., Amlodipine besylate, Felodipine, Isradipine, Nicardipine, Nifedipine, and Nisoldipine); ACE inhibitors (benazepril hydrochloride, Captopril, Enalapril maleate, Fosinopril sodium, Lisinopril, Moexipril, Quinapril hydrochloride, Ramipril, Trandolapril); Angiotensin II receptor blockers (e.g., Losartan potassium, Valsartan, and Irbesartan); and combinations thereof. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating hypertension in a subject compared to administration of one of these agents alone.

Carr et al. (The Journal of Clinical Endocrinology & Metabolism (2004) Vol. 89, No. 6 2601-2607) discusses a link between being overweight or obese and dyslipidemia. Dyslipidemia is typically treated with statins. Statins, HMG-CoA reductase inhibitors, slow down production of cholesterol in a subject and/or remove cholesterol buildup from arteries. Statins include mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating dyslipidemia in a subject compared to administration of one of these agents alone.

Eckel (Circulation (1997) 96:3248-3250) discusses a link between being overweight or obese and ischemic heart disease. Agents administered to treat ischemic heart disease include statins, nitrates (e.g., Isosorbide Dinitrate and Isosorbide Mononitrate), beta-blockers, and calcium channel antagonists. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating ischemic heart disease in a subject compared to administration of one of these agents alone.

Wong et al. (Nature Clinical Practice Cardiovascular Medicine (2007) 4:436-443) discusses a link between being overweight or obese and cardiomyopathy. Agents administered to treat cardiomyopathy include inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating cardiomyopathy in a subject compared to administration of one of these agents alone.

Yusef et al. (Lancet (2005) 366(9497):1640-1649) discusses a link between being overweight or obese and cardiac infarction. Agents administered to treat cardiac infarction include ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase). These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating cardiac infarction in a subject compared to administration of one of these agents alone.

Suk et al. (Stroke (2003) 34:1586-1592) discusses a link between being overweight or obese and strokes. Agents administered to treat strokes include anti-platelet agents (e.g., Aspirin, Clopidogrel, Dipyridamole, and Ticlopidine), anti-coagulant agents (e.g., Heparin), and thrombolytic agents. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating strokes in a subject compared to administration of one of these agents alone.

Stein et al. (The American Journal of Medicine (2005) 18(9):978-980) discusses a link between being overweight or obese and venous thromboembolic disease. Agents administered to treat venous thromboembolic disease include anti-platelet agents, anticoagulant agents, and thrombolytic agents. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating venous thromboembolic disease in a subject compared to administration of one of these agents alone.

Sztrymf et al. (Rev Pneumol Clin (2002) 58(2):104-10) discusses a link between being overweight or obese and pulmonary hypertension. Agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating pulmonary hypertension in a subject compared to administration of one of these agents alone.

Respiratory disorders and conditions such as obesity-hypoventilation syndrome, asthma, and obstructive sleep apnea, have been linked to being overweight or obese. Elamin (Chest (2004) 125:1972-1974) discusses a link between being overweight or obese and asthma. Agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating asthma in a subject compared to administration of one of these agents alone.

Kessler et al. (Eur Respir J (1996) 9:787-794) discusses a link between being overweight or obese and obstructive sleep apnea. Agents administered to treat sleep apnea include Modafinil and amphetamines. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating obstructive sleep apnea in a subject compared to administration of one of these agents alone.

Hepatic disorders and conditions, such as nonalcoholic fatty liver disease, have been linked to being overweight or obese. Tolman et al. (Ther Clin Risk Manag (2007) 6:1153-1163) discusses a link between being overweight or obese and nonalcoholic fatty liver disease. Agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating nonalcoholic fatty liver disease in a subject compared to administration of one of these agents alone.

Skeletal disorders and conditions, such as back pain and osteoarthritis of weight-bearing joints, have been linked to being overweight or obese. van Saase (J Rheumatol (1988) 15(7):1152-1158) discusses a link between being overweight or obese and osteoarthritis of weight-bearing joints. Agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating osteoarthritis of weight-bearing joints in a subject compared to administration of one of these agents alone.

Metabolic disorders and conditions, for example, Prader-Willi Syndrome and polycystic ovary syndrome, have been linked to being overweight or obese. Cassidy (Journal of Medical Genetics (1997) 34:917-923) discusses a link between being overweight or obese and Prader-Willi Syndrome. Agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax). These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating Prader-Willi Syndrome in a subject compared to administration of one of these agents alone.

Hoeger (Obstetrics and Gynecology Clinics of North America (2001) 28(1):85-97) discusses a link between being overweight or obese and polycystic ovary syndrome. Agents administered to treat polycystic ovary syndrome include insulin-sensitizers, combinations of synthetic estrogen and progesterone, Spironolactone, Eflornithine, and Clomiphene. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating polycystic ovary syndrome in a subject compared to administration of one of these agents alone.

Reproductive disorders and conditions such as sexual dysfunction, erectile dysfunction, infertility, obstetric complications, and fetal abnormalities, have been linked to being overweight or obese. Larsen et al. (Int J Obes (Lond) (2007) 8:1189-1198) discusses a link between being overweight or obese and sexual dysfunction. Chung et al. (Eur Urol (1999) 36(1):68-70) discusses a link between being overweight or obese and erectile dysfunction. Agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating erectile dysfunction in a subject compared to administration of one of these agents alone.

Pasquali et al. (Hum Reprod (1997) 1:82-87) discusses a link between being overweight or obese and infertility. Agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating infertility in a subject compared to administration of one of these agents alone.

Weiss et al. (American Journal of Obstetrics and Gynecology (2004) 190(4): 1091-1097) discusses a link between being overweight or obese and obstetric complications. Agents administered to treat obstetric complications include Bupivacaine hydrochloride, Dinoprostone PGE2, Meperidine HC1, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating obstetric complications in a subject compared to administration of one of these agents alone.

Psychiatric disorders and conditions, for example, weight-associated depression and anxiety, have been linked to being overweight or obese. Dixson et al. (Arch Intern Med (2003) 163:2058-2065) discusses a link between being overweight or obese and depression. Agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate). These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating depression in a subject compared to administration of one of these agents alone.

Simon et al. (Archives of General Psychiatry (2006) 63(7): 824-830) discusses a link between being overweight or obese and anxiety. Agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers. These compounds are administered in regimens and at dosages known in the art. Administering fumagillin, fumagillol, or fumagillin ketone, or derivatives thereof, or salts, esters or prodrugs of these, in combination with at least one of these agents results in weight loss, and provides an increased benefit in ameliorating, arresting development of or eliminating anxiety in a subject compared to administration of one of these agents alone.

Another aspect of the invention provides methods for facilitating and maintaining weight loss in a subject involving administering to the subject an amount of fumagillin, fumagillol, or fumagillin ketone, or derivatives thereof, or salts, esters or prodrugs of these, effective to result in weight loss in the subject; and administering a therapeutically effective amount of a weight loss agent to maintain a reduced weight in the subject.

Weight loss agents include serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, and topamax. These compounds are administered in regimens and at dosages known in the art.

The administration can be performed simultaneously or sequentially. In certain embodiments, fumagillin, fumagillol, or fumagillin ketone, or derivatives thereof, or salts, esters or prodrugs of these is intravenously administered followed by oral administration of the weight loss agent. An exemplary treatment regimen includes a course of intravenous administration of fumagillin, fumagillol, or fumagillin ketone, or derivatives thereof, or salts, esters or prodrugs of these for a period of a few months (for example, 3 months, 4 months, 5 months, 8 months, 10 months. 15 months, etc.) in order to obtain weight loss, followed by a course of oral administration of the weight loss agent to maintain a reduced weight in the subject.

In another aspect, the invention provides methods for treating an overweight or obese subject involving determining a level of at least one biomarker related to being overweight or obese in the subject, and administering an amount of fumagillin, fumagillol, or fumagillin ketone, or derivatives thereof, or salts, esters or prodrugs of these, effective to achieve a target level in the subject. Exemplary biomarkers include body weight, Body Mass Index (BMI), Waist/Hip ratio WHR, plasma adipokines, and a combination of two or more thereof.

Plasma adipokines refer to polypeptide growth factors and cytokines produced substantially by white adipose tissue, pre-adipocytes, and mature adipocytes. Exemplary plasma adipokines include adipsin, adiponectin, leptin, vascular endothelial growth factor, hepatocyte growth factor, tumor necrosis factor alpha, heparin binding epidermal growth factor-like growth factor, interleukin-6 and -8, plasminogen activator inhibitor-1, tissue factor, transforming growth factor beta, macrophage colony-stimulating factor, nerve growth factor, estrogens, leukemia inhibitory factor, lipoprotein lipase, acylation stimulating protein, angiotensin 11, cathepsin D/G, metallothionein-1, bone morphogenetic protein GDF-2, FIZZI, resistin, heparin-binding epidermal growth factor, osteonectin, and hevin, with others listed in Maeda et al. (Gene (1997) 190:227-235).

Adipokine levels are generally related to obesity. Flier et al. (Science (1987), 237(4813):405-408) discusses a link between being overweight or obese and adipsin. Yang (Obesity Research (2002) 10:1104-1110) discusses a link between being overweight or obese and adiponectin. Goossens (International Journal of Obesity (2007) 31:382-384) discusses a link between being overweight or obese and angiotensin II. Chen et al. (Nat Biotechnol. (2003) 3:294-301) discusses a link between being overweight or obese and BMP-9. Nadler (PNAS (2000), 97(21):11371-11376) discusses a link between being overweight or obese and cathepsins. Heine et al. (PNAS (2000) 97:12729-12734) discusses a link between being overweight or obese and estrogen. Harrington et al. (Obesity (2007) 15:563-571) discusses a link between being overweight or obese and epidermal growth factor. Matsumoto et al. (Biochem. Biophys. Res. Commun. (2002) 292:781-786) discusses a link between being overweight or obese and HB-EGF. Tartare-Deckert et al. (J. Biol. Chem. (2002) 276 (25):22231-22237) discusses a link between being overweight or obese and hevin and osteonectin. Rehman et al. (J Am Coll Cardiol (2003) 41:1408-1413) discusses a link between being overweight or obese and HGF and VEGF. Wallenius et al. (Nat Med. (2002) 1:75-79) discusses a link between being overweight or obese and IL-6. Madan et al. (Obes Surg. (2006) 10:1342-50) discusses a link between being overweight or obese and IL-8. Farooqi et al. (J Clin Invest. (2002) 110(8): 1093-1103) discusses a link between being overweight or obese and leptin. Beretta et al. (Peptides (2002) 5:975-984) discusses a link between being overweight or obese and LIF. Nilsson-Ehle (Int J Obes. (1981) 5(6):695-699) discusses a link between being overweight or obese and lipoprotein lipase. Levine et al. (J Clin Invest. (1998) 101(8): 1557-1564) discusses a link between being overweight or obese and M-CSF. Beattie et al. (PNAS (1998) 95(1):358-363) discusses a link between being overweight or obese and metallothionein-1. Nisoli et al. (Endocrinology (1996) 137: 495-503) discusses a link between being overweight or obese and NGF. Kusminski (Clinical Science (2005) 109:243-256) discusses a link between being overweight or obese and resistin. Hotamisligil et al. (J Clin Invest. (1995) 5:2409-2415) discusses a link between being overweight or obese and TNFα. Torun et al. (International Heart Journal (2007) 48(6): 733-741) discusses a link between being overweight or obese and TGFβ. Mutch et al. (Proceedings of the Nutrition Society (2001) 60:341-347) discusses a link between being overweight or obese and plasminogen activator inhibitor-1. Klein et al. (The Journal of Clinical Endocrinology & Metabolism (1998) 83(10):3469-3475) discusses a link between being overweight or obese and estradiol.

Adipokine levels are easily determined using assays known in the art, for example adipokine ELISA kits (commercially available B-Bridge International, Mountain View, Calif.). Additionally, RayBiotech, Inc. (Norcross, Ga.) provides two different commercial adipokine assay that detect numerous different adipokines (RayBio® Biotin Label-based Human Adipokine Antibody Array 1, product numbers AAH-BLG-AD1-2 and AAH-BLG-AD1-4).

By determining a level of a biomarker related to an overweight or obese subject, methods of the invention allow for tailoring treatment to a particular subject, thus avoiding harmful side-effects (e.g., wasting) associated with administering fumagillin at higher dosages, such as dosages intended to treat cancer (Ingbar et al. (Nature (1990) 348:555-557); see also D'Amato et al. (U.S. Pat. No. 6,017,949) and BaMaung et al. (U.S. Pat. No. 6,323,228)).

Dosage and administration are adjusted to provide effective levels of fumagillin, fumagillol, or fumagillin ketone, or derivatives thereof, or salts, esters or prodrugs of these, to achieve the target level of the biomarker. The target level includes an increase in the level of the biomarker or a decrease in the level of the biomarker compared to the level of the biomarker in the overweight or obese subject prior to administration of fumagillin, fumagillol, or fumagillin ketone, or derivatives thereof, or salts, esters or prodrugs of these. The target level depends on the particular biomarker. For example, if the biomarker used is BMI, the target level may be decreasing a subject's BMI to a range from about 18.5 kg/m$^2$ to about 24.9 kg/M$^2$, the CDC definition of normal weight range.

If the biomarker is a plasma adipokine, the target level depends on the relationship between the level of the adipokine and obesity. For example, adipsin levels are shown to be decreased in an overweight or obese subject (Flier et al. (Science (1987), 237(4813):405-408). Achieving a target level of adipsin is increasing the level of adipsin in an overweight or obese subject to a desired level. In contrast, HB-EGF levels are shown to be increased in an overweight or obese subject (Matsumoto et al., Biochem. Biophys. Res. Commun. (2002) 292:781-786). Achieving a target level of HB-EGF is decreasing the level of HB-EGF in an overweight or obese subject to a desired level. Relationships among various adipokines and obesity are described above. One of skill in the art, with the knowledge of the disclosure, will be able to determine the target level of the adipokine to be achieved.

In another aspect, the invention provides enteral pharmaceutical formulations including fumagillin, fumagillol, or fumagillin ketone, or derivatives thereof, or salts, esters or prodrugs of these; an enteric material; and a pharmaceutically acceptable carrier or excipient thereof. To take advantage of the discovery that fumagillin, fumagillol, or fumagillin ketone, or derivatives thereof, or salts, esters or prodrugs of these, demonstrate a larger absorption profile in a small intestine, the formulations further include an enteric material, therefore improving the bioavailability of fumagillin, fumagillol, or fumagillin ketone, or derivatives thereof, or salts, esters or prodrugs of these. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0.

Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleat, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

In certain embodiments, formulations of the invention includes two or more enteric polymers that are soluble at different pHs. For example, pharmaceutical formulations of the invention may contain two or more enteric materials, provided at least two of the materials have solubilities at different pHs. For instance, the pharmaceutical formulation may include a coating including an enteric material that dissolves at a pH of about 5.5, of about 5.7, of about 5.9, of about 6.1, of about 6.3, or of about 6.5, and a second enteric material that dissolves at a different pH in the small intestine, such as a pH of about 7.0, of about 7.2, of about 7.4, of about 7.6, of about 7.8, or of about 8.0.

A coating can also have three enteric materials each of which will dissolve at a different pH in the small intestine. For example, hydroxypropyl methylcellulose phthalate (HPMCP), polyvinyl acetate phthalate (PVAP) and Coateric will dissolve in buffers of pH of about 5.0 and higher. Eudragit L100-55, Eudragit L30D-55, Kollicoat EMM30D, and Estacryl 30D will dissolve from a pH of about 5.5 to a pH of about 6.5. Cellulose acetate phthalate (CAP) and Aquateric will dissolve in buffers above about a pH of 6.2. Eudragit S100 and FS30D will dissolve at a pH of about 7.0 to a pH of about 7.5. Additional mixtures of enteric materials and methods of making an enteric coating having more than one enteric material are shown in Chang et al. (WO/2004/062577).

Formulations of the invention can also include a surfactant, to assist in uptake of fumagillin, fumagillol, or fumagillin ketone, or derivatives thereof, or salts, esters or prodrugs of these, into the intestinal mucosa. Surfactants may be anionic, cationic, amphoteric or nonionic surface active agents. Suitable anionic surfactants include compounds containing carboxylate, sulfonate and sulfate ions. The anionic or amphoteric surfactants may be present as pharmaceutically acceptable salts, including for example sodium, potassium, ammonium salts. Examples of anionic surfactants include long chain alkyl sulfonates and alkyl aryl sulfonates such as sodium dodecylbenzene sulfonate; dialkyl sodium sulfosuccinates, such as sodium bis-(2-ethylthioxyl)-sulfosuccinate; and alkyl sulfates such as sodium lauryl sulfate.

Cationic surfactants include quaternary ammonium compounds such as benzalkonium chloride, benzethonium chloride, cetrimonium bromide, stearyl dimethylbenzyl ammonium chloride, and cocoamine. Examples of nonionic surfactants include polyoxyethylene, ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, poloxamer 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

Enteral formulations of the invention may be administered using any amount and any route of administration effective for treating an overweight or obese subject, as described herein.

In another aspect, the invention provides pharmaceutical formulations comprising fumagillin, fumagillol, or fumagillin ketone, or derivatives thereof, or salts, esters or prodrugs of these; and a pharmaceutically acceptable carrier or excipient thereof that is suitable for oral cavity administration. Examples of oral cavity administration include buccal administration and sublingual administration.

Formulations of the invention can also include a surfactant, to assist in uptake of fumagillin, fumagillol, or fumagillin ketone, or derivatives thereof, or salts, esters or prodrugs of these, into oral mucosa. Surfactants may be anionic, cationic, amphoteric or nonionic surface active agents. Suitable anionic surfactants include compounds containing carboxylate, sulfonate and sulfate ions. The anionic or amphoteric surfactants may be present as pharmaceutically acceptable salts, including for example sodium, potassium, ammonium salts. Examples of anionic surfactants include long chain alkyl sulfonates and alkyl aryl sulfonates such as sodium dodecylbenzene sulfonate; dialkyl sodium sulfosuccinates, such as sodium bis-(2-ethylthioxyl)-sulfosuccinate; and alkyl sulfates such as sodium lauryl sulfate.

Cationic surfactants include quaternary ammonium compounds such as benzalkonium chloride, benzethonium chloride, cetrimonium bromide, stearyl dimethylbenzyl ammonium chloride, and cocoamine. Examples of nonionic surfactants include polyoxyethylene, ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, poloxamer 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

Oral cavity formulations of the invention may be administered using any amount and any route of administration effective for treating an overweight or obese subject, as described herein. In particular for the oral cavity formulations herein, to improve the bioavailability of fumagillin, fumagillol, or fumagillin ketone, or derivatives thereof, or salts, esters or prodrugs of these, the invention provides formulations that include a pharmaceutically acceptable carrier or excipient thereof that is suitable for oral cavity administration. In particular, the invention provides formulations that include a pharmaceutically acceptable carrier or excipient thereof for buccal administration or sublingual administration. The formulation for buccal administration or sublingual administration can be in a form of a tablet, a lozenge, a wafer, and an ointment. Tablets, lozenges, or wafers are placed between the cheek and gingival (buccal) or under the tongue (sublingual) and allowed to dissolve. The drug, i.e., fumagillin, fumagillol, or fumagillin ketone, or derivatives thereof, or salts, esters or prodrugs of these, is absorbed through the oral mucous membrane and enters the systemic circulation, bypassing the portal circulation. An advantage of the tablets, lozenges, or wafers is in the efficient absorption of the drug, because the drug is not decomposed by the liver.

In embodiments in which the formulation is in the form of a tablet, a lozenge, or a wafer, the carrier or excipient thereof is a water soluble or water dispersible carrier material. Exemplary water soluble or water dispersible carrier materials include polysaccharides (e.g., microcrystalline cellulose, mannitol, anhydrous lactose, crystalline lactose, spray-dried lactose, amylose, or sorbitol), polyvinylalcohol, polyvinylpyrrolidine, cellulose derivatives (e.g., methyl cellulose, hydroxyethyl cellulose, hydroxypropylmethyl cellulose or hydroxypropyl cellulose), gelatin, and mixtures thereof.

Oral dosage forms of tablets, lozenges, or wafers are prepared using any suitable process known to the art. See, for example, Remington's Pharmaceutical Sciences, 18th Edition, A. Gennaro, Ed., Mack Pub. Co. (Easton, Pa. 1990), Chapters 89-91, which is hereby incorporated by reference. Typically, fumagillin, fumagillol, or fumagillin ketone, or derivatives thereof, or salts, esters or prodrugs of these, is mixed with the water soluble or water dispersible carrier materials and compressed into tablets. The oral dosage form can be prepared by combining the water soluble or water dispersible carrier materials, with fumagillin, fumagillol, or fumagillin ketone, or derivatives thereof, or salts, esters or prodrugs of these, together with any other excipients for the tableting or capsule filling of beadles, using for instance a wet granulation technique or a direct compression method, to form a uniform granulate.

Alternatively, fumagillin, fumagillol, or fumagillin ketone, or derivatives thereof, or salts, esters or prodrugs of these, can be mixed with the granulate after the granulate is prepared. The moist granulated mass with or without fumagillin, fumagillol, or fumagillin ketone, or derivatives thereof, or salts, esters or prodrugs of these, is then dried and sized using a suitable screening device to provide a powder, which can then be filled into capsules or compressed into tablets or caplets, as desired.

More particularly, in a wet granulation method, fumagillin, fumagillol, or fumagillin ketone, or derivatives thereof, or salts, esters or prodrugs of these, and the water soluble or water dispersible carrier materials and other ingredients are granulated in a granulating fluid (e.g., isopropyl alcohol, ethyl alcohol, and water) in a planetary mixer, high shear mixer, or a fluidized bed granulator. Binding agents may be contained in the granulating fluid or in the dry mix of ingredients. The wet granules are dried in an oven or a fluidized bed dryer, and then sieved through a suitable screen to obtain free flowing granules. The resulting granules may be blended with a suitable lubricant and glidant, and the lubricated granules are compressed into tablets on a rotary press using appropriate tooling.

In a direct compression method, fumagillin, fumagillol, or fumagillin ketone, or derivatives thereof, or salts, esters or prodrugs of these, the water soluble or water dispersible carrier materials and other ingredients are sieved through a stainless steel screen, such as a 40 mesh steel screen. The sieved materials are then charged to a suitable blender and blended for about ten minutes with an intensifier bar for about three minutes. The blend is then compressed into tablets on a rotary press using appropriate tooling.

Such dosage forms may also comprise, as is normal practice, additional substances other than inert diluents, e.g., tableting lubricants and other tableting aids such a magnesium stearate and microcrystalline cellulose. Additional agents include pigments, colorants, stabilizing agents, plasticizers, and glidants.

Formulations of the invention can further include adhesives as described in Tanaka et al. (U.S. Pat. No. 4,059,686). Formulations of the invention can also include flavoring agents. Suitable flavoring agents to be added to generate a sour taste include an organic acid such as citric acid, tartaric acid, or fumaric acid. Suitable flavoring agents to be added to generate a sweet taste include saccharine (synthetic sweetner) or glycyrrhizin (natural sweetner).

In embodiments in which the formulation is in the form of an ointment, the carrier or excipient thereof provides a base for the ointment and can include, for example, white petrolatum, polyethylene glycol, a compatible mixture of peanut oil or purified sesame oil with beeswax, or a compatible mixture of polyethylene and liquid paraffin. Further, if necessary, there are used nonionic surface active agents such as polyoxyethylene fatty acid esters, polyoxyethylene higher alcohol ethers, polyoxyethylene sorbitan fatty acid esters, and glyceryl fatty acid monoesters and additives such as anhydrous lanolin, cholesterol, squalene, and acetyl alcohol. Fumagillin, fumagillol, or fumagillin ketone, or derivatives thereof, or salts, esters or prodrugs of these, are added to the ointment base, and the ointment base and fumagillin, fumagillol, or fumagillin ketone, or derivatives thereof, or salts, esters or prodrugs of these, are kneaded together to generate the ointment formulation.

The invention having now been described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims.

The contents of all references and citations, including issued patents, published patent applications, and journal articles cited throughout this application, are hereby incorporated by reference in their entireties for all purposes.

EXAMPLES

Example 1

Fumagillin binding to MetAP-2 in Adipose Tissue of Obese Mice

Fumagillin is an anti-angiogenic compound that binds to the MetAP-2 protein. A study was designed to determine whether fumagillin binds MetAP-2 in adipose tissue. The results show that fumagillin binds MetAP-2 in adipose tissue.

Diet-induced obese mice were orally (p.o.) administered fumagillin (3 mg/kg or 10 mg/kg; Medivet), subcutaneously administered (s.c.) TNP-470 (1 mg/kg, 3 mg/kg, 10 mg/kg, or 30 mg/kg; synthesized by standard semi-synthetic processes as described in European Patent EP 0 357 061), or administered a solution of 10% dimethyl sulfoxide (DMSO; control; Sigma-Aldrich). Mice were sacrificed and adipose tissue samples were obtained.

An ELISA assay of MetAP-2 binding was conducted with tissue lysates prepared from the adipose tissue samples. The MetAP-2 ELISA is a quantitative assay to determine the amount of free MetAP-2 in tissue or cell lysates, i.e., MetAP-2 not covalently bound to fumagillin or TNP-470. The assay takes advantage of the fact that biotinylated fumagillin can bind to the catalytic site of the MetAP-2 enzyme only if this site has not already been derivatized by fumagillin or TNP-470. The biotinylated MetAP-2-inhibitor complex was captured on a streptavidin-coated plate and detected with a rabbit anti-MetAP-2 antibody (Zymed Laboratories Inc.). Horseradish peroxidase-conjugated anti-rabbit immunoglobulin G (IgG) was added to detect the MetAP-2 antibody immobilized to the streptavidin-coated plate with its covalently bound biotinylated fumagillin. Tetramethylbenzidine (TMB) substrate was added and the reaction was stopped by addition of sulfuric acid. Analysis was performed by determining absorption at 450 nm. Human recombinant MetAP-2 (R&D Systems), pre-bound to biotinylated fumagillin, was used to generate a standard curve.

Data show that fumagillin administered orally at 3 mg/kg or 10 mg/kg binds MetAP-2 in adipose tissue (FIG. 1). Data also show that TNP-470 administered subcutaneously at 1 mg/kg, 3 mg/kg, 10 mg/kg, or 30 mg/kg also binds MetAP-2 in a dose dependent manner (FIG. 1). Data further show that at 3 mg/kg and at 10 mg/kg there is greater binding of subcutaneously administered TNP-470 to MetAP-2 in adipose tissue compared to binding of orally administered fumagillin to MetAP-2 in adipose tissue at the same dosages.

Based on the results, studies were undertaken to analyze effects of fumagillin on weight loss, as shown in Examples below.

Example 2

Orally Administered Fumagillin Causes Weight Loss in Diet-Induced Obese Mice

Based on data shown in Example 1, a weight loss study was conducted in obese mice. The mice in this study were not genetically obese, but prior to and during the study, obesity was induced by a high-fat diet. Twelve week-old C57BL/6NTac mice, maintained on a 60% fat diet prior to and during the study, were separated into six groups, eight animals per group. Average body weight of the mice was 38 g at the start of the study.

Fumagillin was administered to four of the diet-induced obese mice groups by oral gavage as a solution in 10% DMSO, at doses of 1 mg/kg/day, 3 mg/kg/day, 10 mg/kg/day and 30 mg/kg/day respectively, for 28 days. A fifth group received 10% DMSO vehicle-only (control) by oral gavage, and the sixth group received neither vehicle nor fumagillin (naïve). Body weight was measured on day 0 (pre-study) and subsequently on day 3, day 8, day 15, day 22, and day 29 of the study. Daily food consumption was also recorded.

Figure 2:
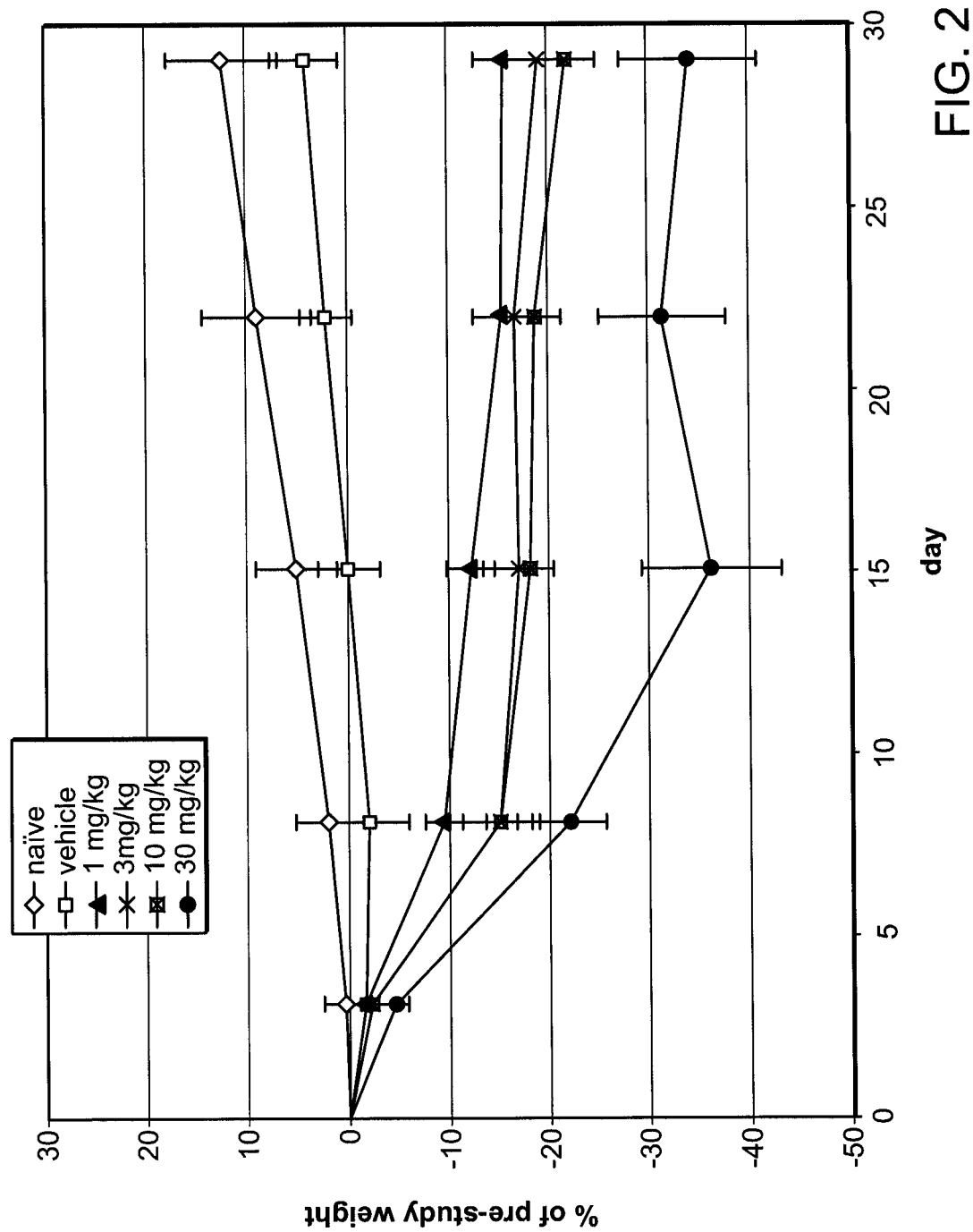
FIG. 2 is a line graph showing effects of fumagillin administered orally at different dosages on weight of mice over a 30 day period of time. Data is expressed as percent of pre-study weight.
Figure 3:
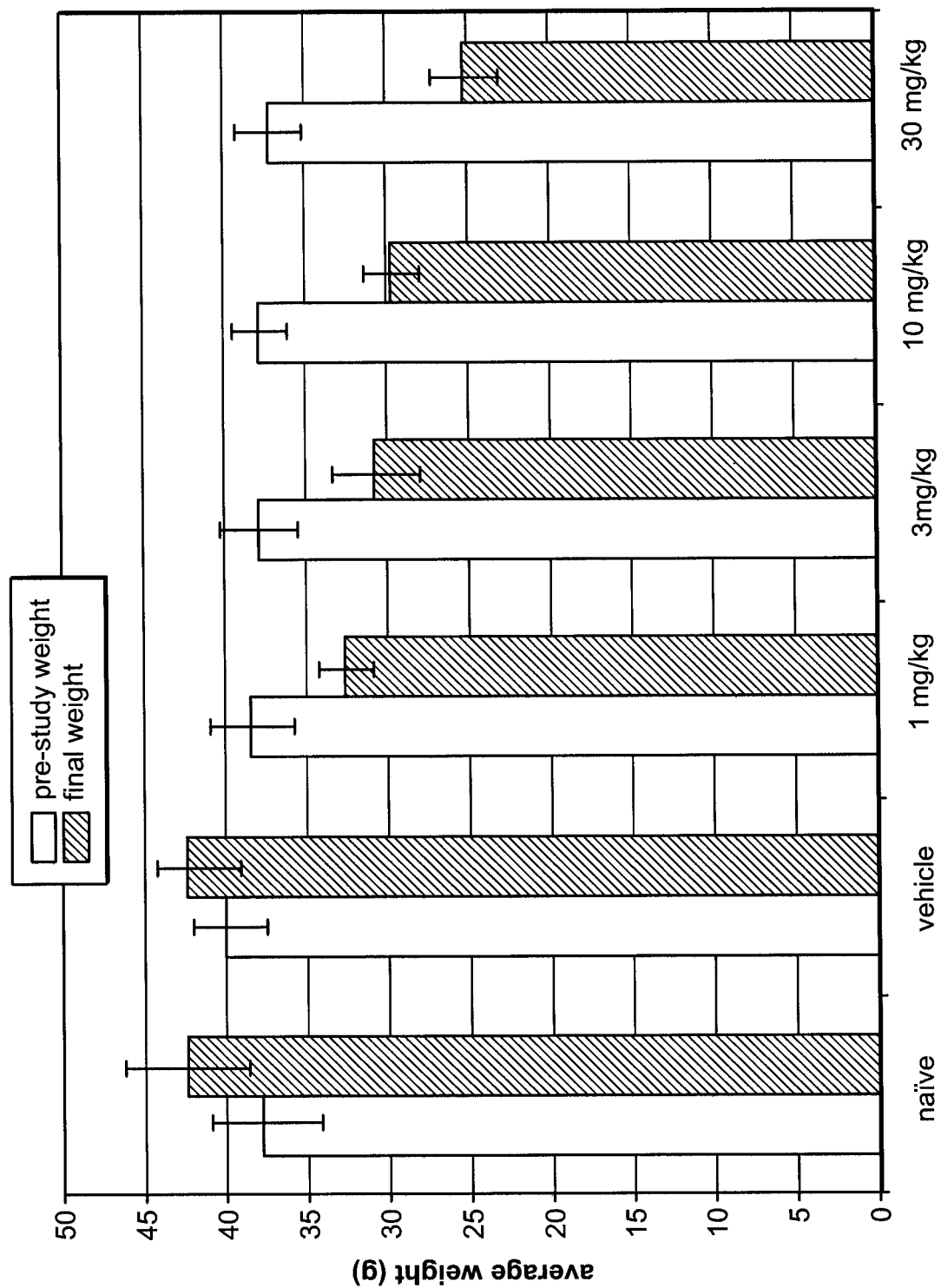
FIG. 3 is a bar graph showing effects of fumagillin administered orally at different dosages on weight of mice over a 30 day period of time. Data is expressed as average weight of mice in grams.
Figure 4:
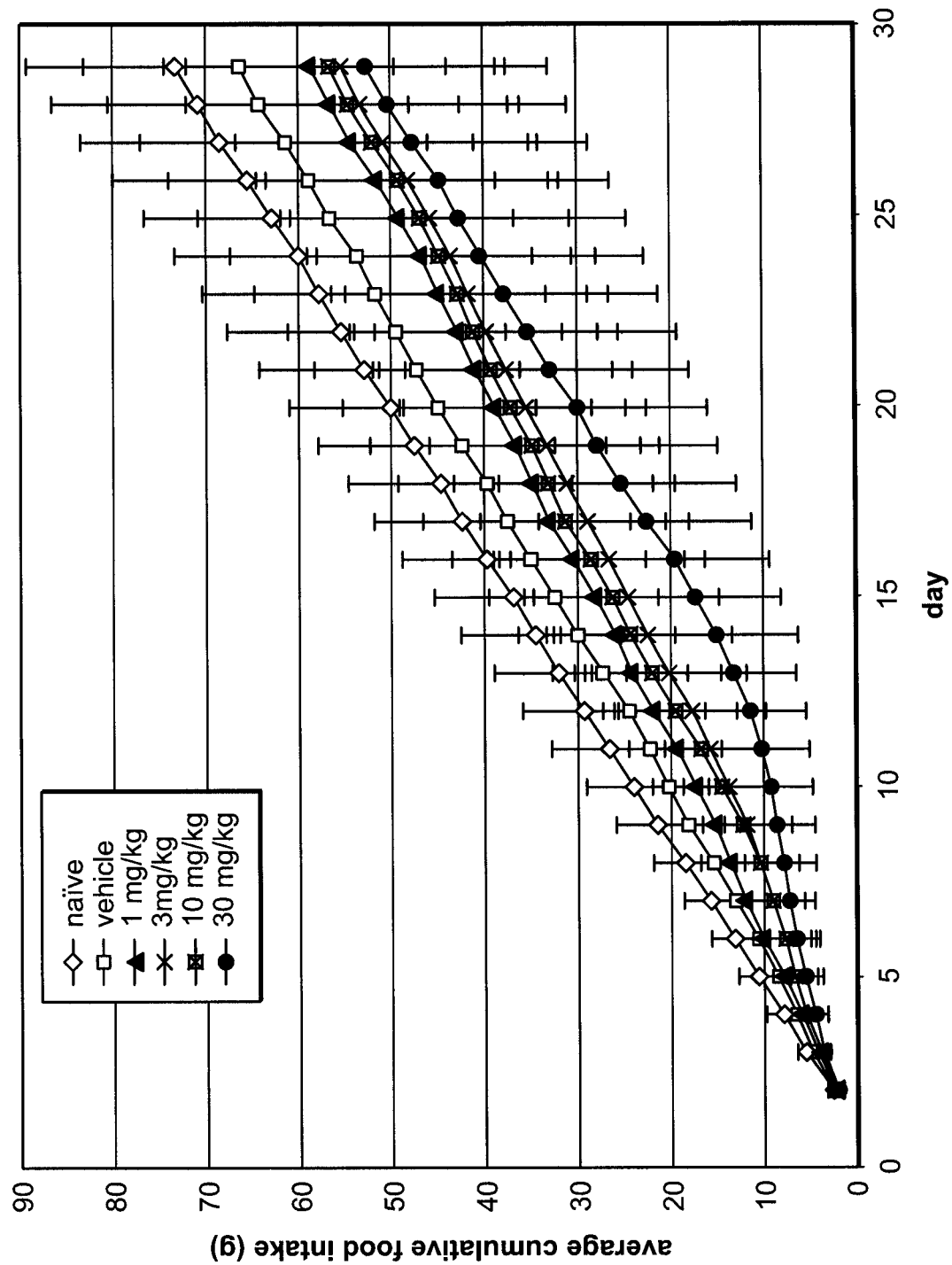
FIG. 4 is a line graph showing effects of fumagillin administered orally at different dosages on food intake of mice over a 30 day period of time. Data is expressed as average cumulative food intake in grams.

Data show that mice administered fumagillin at any of the dosages (1 mg/kg/day, 3 mg/kg/day, 10 mg/kg/day, and 30 mg/kg/day) lost weight over the course of the 30 days (FIGS. 2 and 3). In contrast, naïve mice and control mice administered vehicle-only gained weight over the course of the 30 days (FIGS. 2 and 3). A dose-related weight loss response to fumagillin was observed (FIGS. 2 and 3). Data further show that mice administered fumagillin consumed less food than vehicle-only mice and naïve mice (FIG. 4). Food consumption was related to dosage of fumagillin, with mice receiving a dosage of 30 mg/kg/day consuming the least amount of food over the 30 day period of time (FIG. 4).

Weight losses of 15%, 18%, 21% and 33% were observed by the end of the study for diet-induced obese mice groups receiving 1 mg/kg/day, 3 mg/kg/day, 10 mg/kg/day, and 30 mg/kg/day of fumagillin respectively, as a percentage of pre-study weight (FIGS. 2 and 3). In contrast, data show that the naive group of mice gained 13% of body weight by the end of the study, and that the vehicle-only group of mice gained 5% of body weight by the end of the study. A non-effective dose was not identified, but could be concluded to be below 1 mg/kg/day.

The weight loss at fumagillin doses of 1 mg/kg/day, 3 mg/kg/day, and 10 mg/kg/day was approximately equal to weight gain due to the high-fat diet, i.e., diet-induced weight gain was effectively reversed by fumagillin treatment at these doses.

Additional benefits of fumagillin treatment observed in this study included reductions in both cholesterol and serum glucose levels. Hematology showed a decrease in leukocytes, particularly lymphocytes, in fumagillin dose groups. Neutrophil counts decreased at lower fumagillin doses of 1 mg/kg and 3 mg/kg, and increased at doses of 10 mg/kg and 30 mg/kg, compared to neutrophil counts from vehicle-only mice. No decrease in platelets was observed.

Thus, data herein show that fumagillin is effective for weight reduction in diet-induced obese mice at doses at least as low as 1 mg/kg/day.

Studies were then undertaken to analyze effects of fumagillin on weight loss at lower dosages, as shown in Examples below.

Example 3

Fumagillin Causes Weight Loss in Diet-Induced Obese Mice at Very Low Doses

In view of the surprising data showing a weight loss response to fumagillin at a dose as low as 1 mg/kg/day (See Example 2), a further study was conducted using even lower doses, i.e., 0.1 mg/kg/day and 0.3 mg/kg/day.

Mice were divided into two groups, a diet-induced obese group and a lean group. For the diet-induced obese group, fifteen week-old C57BL/6NTac mice, maintained prior to and during the study on a diet containing 60% fat on a kilocalorie basis, were further separated into six groups, eight animals per group. Average body weight of these diet-induced obese mice was 38 g at the start of the study. For the lean group, fifteen week-old C57BLI6NTac mice, maintained on a diet containing 4.3% by weight fat prior to and during the study, were further separated into two groups, eight animals per group. Average body weight of these lean mice was 28 g at the start of the study.

Fumagillin was administered to three of the diet-induced obese mice groups by oral gavage as a solution in 10% DMSO, at doses of 0.1 mg/kg/day, 0.3 mg/kg/day, and 1 mg/kg/day respectively. A fourth diet-induced obese mice group received the 10% DMSO vehicle only by oral gavage. A group of lean mice was administered fumagillin by oral gavage as a solution in 10% DMSO at a dose of 1 mg/kg/day. Treatments were administered daily for 11 days.

Figure 5:
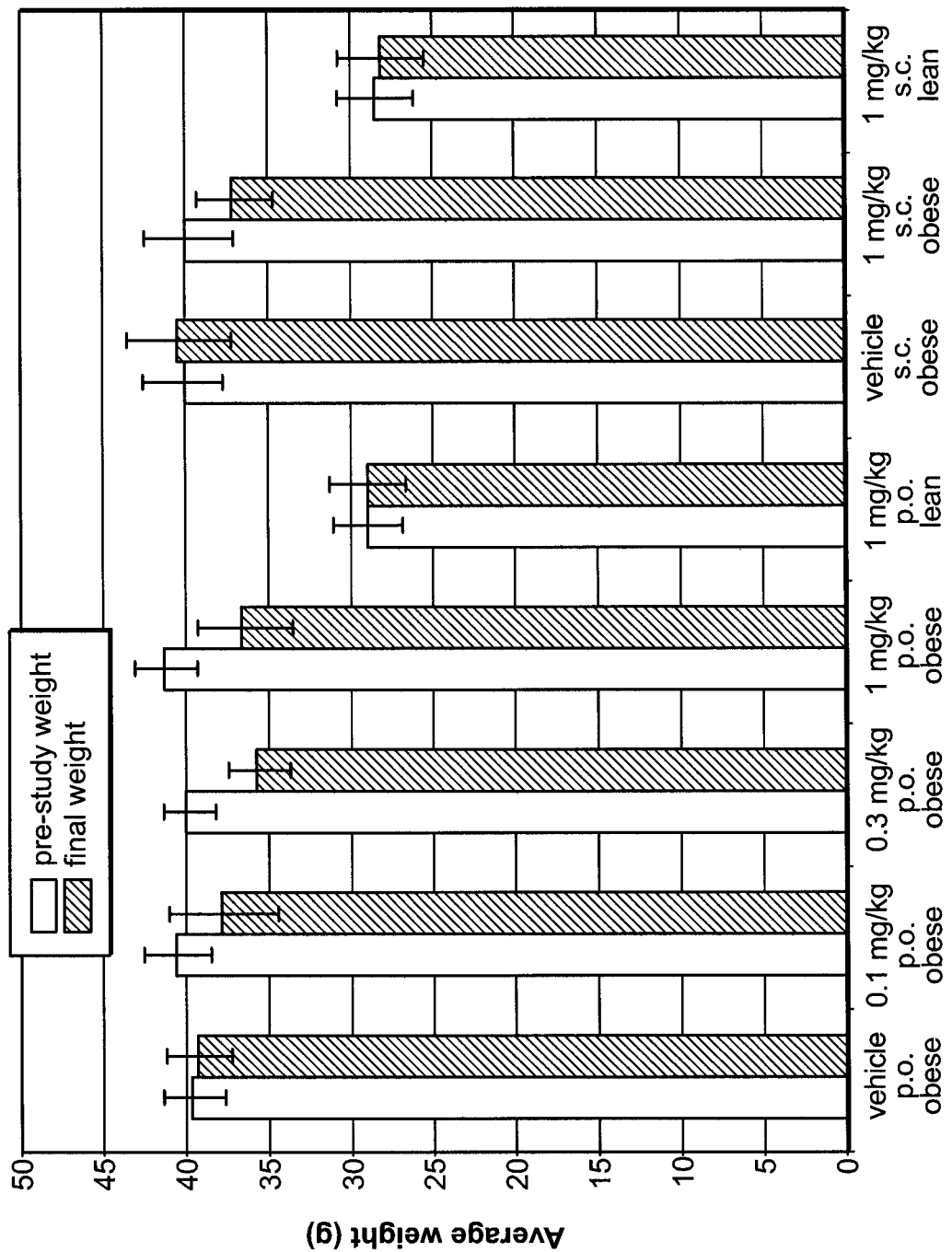
FIG. 5 is a bar graph showing effects of fumagillin administered orally and subcutaneously at different dosages on weight of mice over an 14 day period of time. Data is expressed as average weight of mice in grams.

Data show that mice administered fumagillin at even very low dosages (0.1 mg/kg/day, 0.3 mg/kg/day, and 1 mg/kg/day) lost weight over the course of the 14 days (FIG. 5). A dose-related weight loss response to fumagillin was observed (FIG. 5). Weight losses of 7%, 11% and 12% were observed by the end of the study for diet-induced obese mice groups receiving 0.1 mg/kg/day, 0.3 mg/kg/day, and 1 mg/kg/day of fumagillin respectively, as a percentage of pre-study weight (FIG. 5). A non-effective dose was not identified, but could be concluded to be below 0.1 mg/kg/day.

In contrast, control mice administered vehicle only showed a change in weight that was −1%, a non-significant weight loss (FIG. 5). Lean mice administered 1 mg/kg/day showed no weight change (FIG. 5).

Data herein demonstrate that fumagillin is effective for weight reduction in diet-induced obese mice at even very low doses, such as 0.1 mg/kg/day or lower. A study was then undertaken to analyze whether oral administration compared to subcutaneous administration of fumagillin affected weight loss in diet-induced obese mice.

Example 4

Oral Administration Compared to Subcutaneous Administration

A study was undertaken to analyze whether oral administration compared to subcutaneous administration of fumagillin affected weight loss in diet-induced obese mice. Mice were divided into two groups, a diet-induced obese group and a lean group. For the diet-induced obese group, fifteen week-old C57BL/6NTac mice, maintained prior to and during the study on a diet containing 60% fat on a kilocalorie basis, were further separated into six groups, eight animals per group. Average body weight of these diet-induced obese mice was 38 g at the start of the study. For the lean group, fifteen week-old C57BLI6NTac mice, maintained on a diet containing 4.3% by weight fat prior to and during the study, were further separated into two groups, eight animals per group. Average body weight of these lean mice was 28 g at the start of the study.

Fumagillin was administered to three of the diet-induced obese groups by oral gavage as a solution in 10% DMSO, at doses of 0.1 mg/kg/day, 0.3 mg/kg/day, and 1 mg/kg/day respectively. A fourth diet-induced obese group received the 10% DMSO vehicle-only by oral gavage. A fifth diet-induced obese group received fumagillin at a 1 mg/kg/day dose by subcutaneous injection of a solution in 10% DMSO. A sixth diet-induced obese group received the 10% DMSO vehicle only by subcutaneous injection. A group of lean mice was administered fumagillin by oral gavage as a solution in 10% DMSO at a dose of 1 mg/kg/day.

Another group of lean mice was administered fumagillin by subcutaneous injection of a solution in 10% DMSO at a dose of 1 mg/kg/day. Treatments were administered daily for 14 days.

Data show that fumagillin administered subcutaneously to diet-induced obese mice at 1 mg/kg/day was effective for providing weight loss (FIG. 5). Weight loss of 7% was observed by the end of the study for groups receiving 1 mg/kg/day of fumagillin subcutaneously, as a percentage of pre-study weight (FIG. 5). In contrast, control mice subcutaneously administered vehicle only showed a change in weight that was +1%, a non-significant weight loss (FIG. 5). Further, lean mice subcutaneously administered fumagillin at 1 mg/kg/day also showed no weight loss.

Further, 7%, 11% and 12% weight losses were observed by the end of the study for diet-induced obese mice orally administered 0.1 mg/kg/day, 0.3 mg/kg/day, and 1 mg/kg/day of fumagillin respectively, as a percentage of pre-study weight (FIG. 5). In contrast, control mice orally administered vehicle only showed a change in weight that was −1%, a non-significant weight loss (FIG. 5). Lean mice orally administered 1 mg/kg/day showed no weight change (FIG. 5).

Less weight loss was observed in mice subcutaneously administered fumagillin at 1 mg/kg/day (7%) compared to weight loss observed in mice orally administered fumagillin at 1 mg/kg/day (12%; FIG. 5). In fact, the amount of weight loss observed in the diet-induced obese mice subcutaneously administered fumagillin at 1 mg/kg/day (7%) was comparable to amount of weight loss observed in mice orally administered fumagillin at 0.1 mg/kg/day (7%), one-tenth of the subcutaneous dose (FIG. 5).

The above data demonstrate that oral administration of fumagillin appears to be more efficacious than subcutaneous administration of fumagillin. However, both oral administration and subcutaneous administration of fumagillin result in weight loss in diet-induced obese mice. Further, administration of fumagillin, orally or subcutaneously, at these dosages does not result in weight loss in lean mice.

A study was next designed to further analyze weight loss with respect to lean body mass.

Example 5

Weight Loss Without Substantial Reduction of Lean Body Mass

Lean body mass is important to normal function in subjects. Substantial loss of lean body mass is not a desirable consequence of a therapy for an overweight or obese subject. A study was undertaken to analyze weight loss with respect to lean body mass.

Mice were divided into two groups, a diet-induced obese group and a lean group (control). For the diet-induced obese group, C57BL/6NTac mice maintained prior to and during the study on a diet containing 60% fat on a kilocalorie basis were further divided into two groups, fifteen mice per group. Average body weight of these diet-induced obese mice was 40 g at the start of the study. For the lean group, fifteen C57BLI6NTac mice were maintained on a diet containing 4.3% by weight fat prior to and during the study. Average body weight of these lean mice was 33 g at the start of the study. Daily food consumption was also recorded.

Fumagillin was administered to one of the diet-induced obese mice groups by oral gavage as a solution in 10% DMSO, at dose of 1 mg/kg/day, for 47 days. The other diet-induced obese mice group and the lean mice group were not administered anything.

Figure 6:
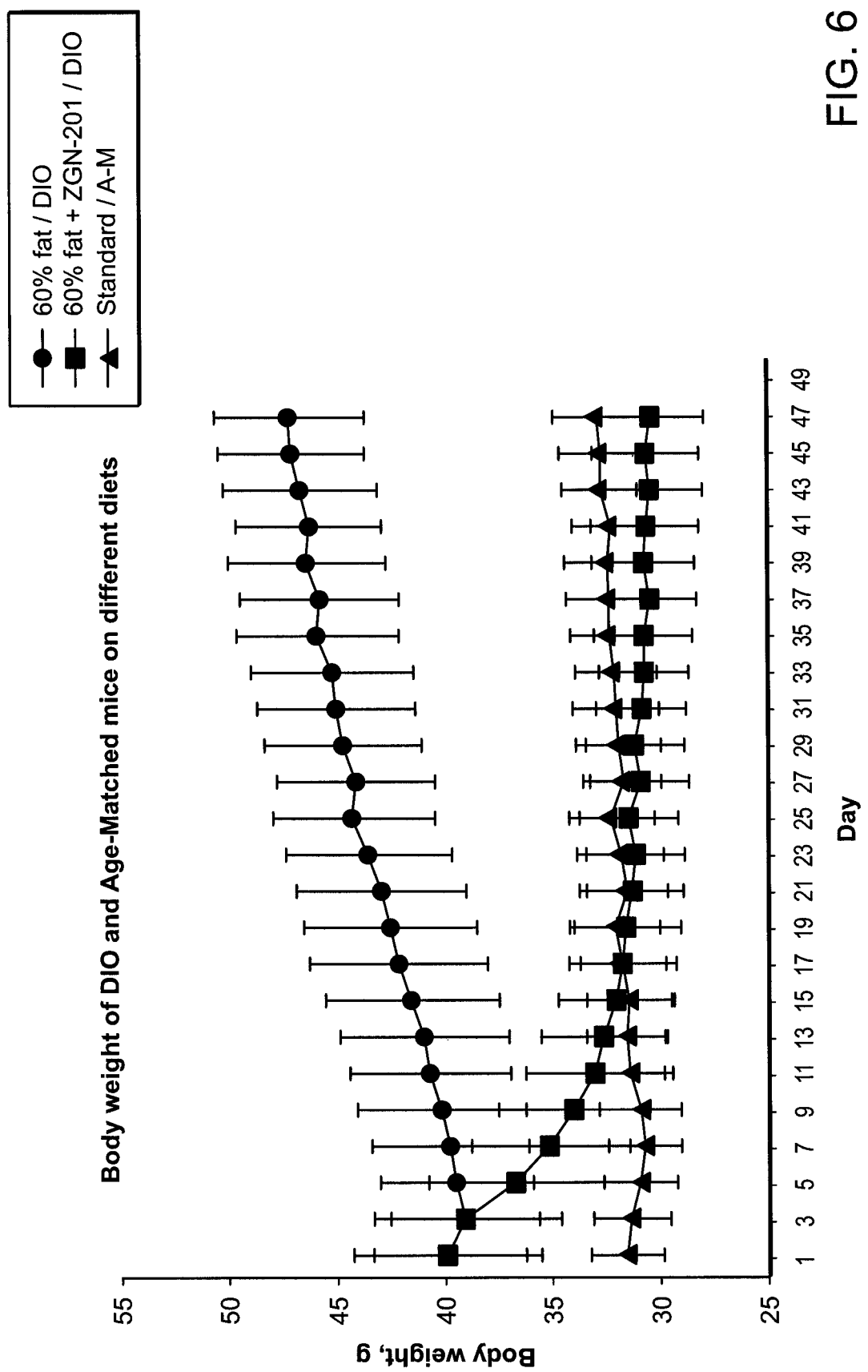
FIG. 6 is a line graph showing effects of fumagillin administered orally on weight of mice over a 47 day period of time. Data is expressed as average weight of mice in grams.

Data show that the diet-induced obese group of mice administered fumagillin lost weight over the first seventeen days of the study (from an average weight of 40 g on day 1 decreasing to an average weight of 32 g on day seventeen) and this group of mice maintained an average weight of approximately 32 g through day 47 of the study (FIG. 6). Further, the diet-induced obese group of mice administered fumagillin had an average weight (32 g) after 47 days that was similar to the average weight of the lean mice group (33 g) after 47 days (FIG. 6). In contrast, the group of diet-induced obese mice that did not receive fumagillin continued to gain weight throughout the 47 days (from an average weight of 40 g on day 1 increasing to an average weight of 46 g on day 47; FIG. 6).

Figure 7:
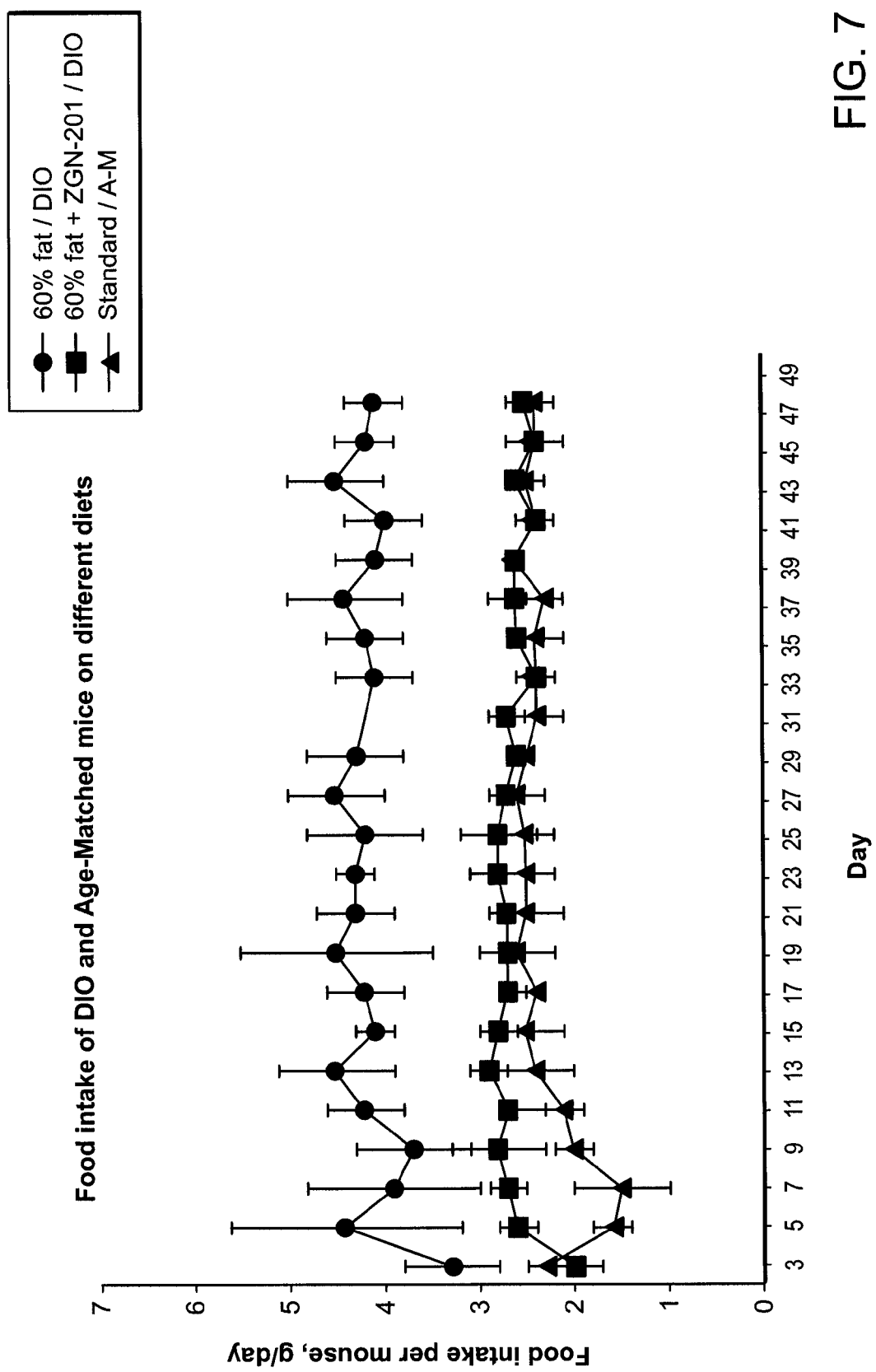
FIG. 7 is a line graph showing effects of fumagillin administered orally on food intake of mice over a 47 day period of time. Data is expressed as average cumulative food intake in grams.

Data further show that the diet-induced obese group of mice administered fumagillin consumed approximately the same amount of food (2.2 g/day) compared to the amount of food consumed by the lean mice group (2.3 g/day) throughout the 47 days (FIG. 7). In contrast, the group of diet-induced obese mice that did not receive fumagillin consumed approximately 4.1 g/day of food.

These data demonstrate that administering fumagillin results in reduced adiposity without substantial reduction of lean body mass because the weight of diet-induced obese mice plateaued at approximately the same weight compared to the weight of the lean mice (FIG. 6).

A study was next designed to further investigate the effect of fumagillin on lean body mass.

Example 6

Effect of Fumagillin on Lean Body Mass

Mice were first divided into three groups, a control group, a diet-induced obese group, and a lean group. For the diet-induced obese group, C57BL6J mice maintained prior to and during the study on a diet containing 40% fat on a kilocalorie basis were further divided into two groups. For the lean group, C57BL6J mice were maintained on a diet containing 4% by weight fat prior to and during the study. Each of the groups was subsequently divided as described below.

Figure 8:
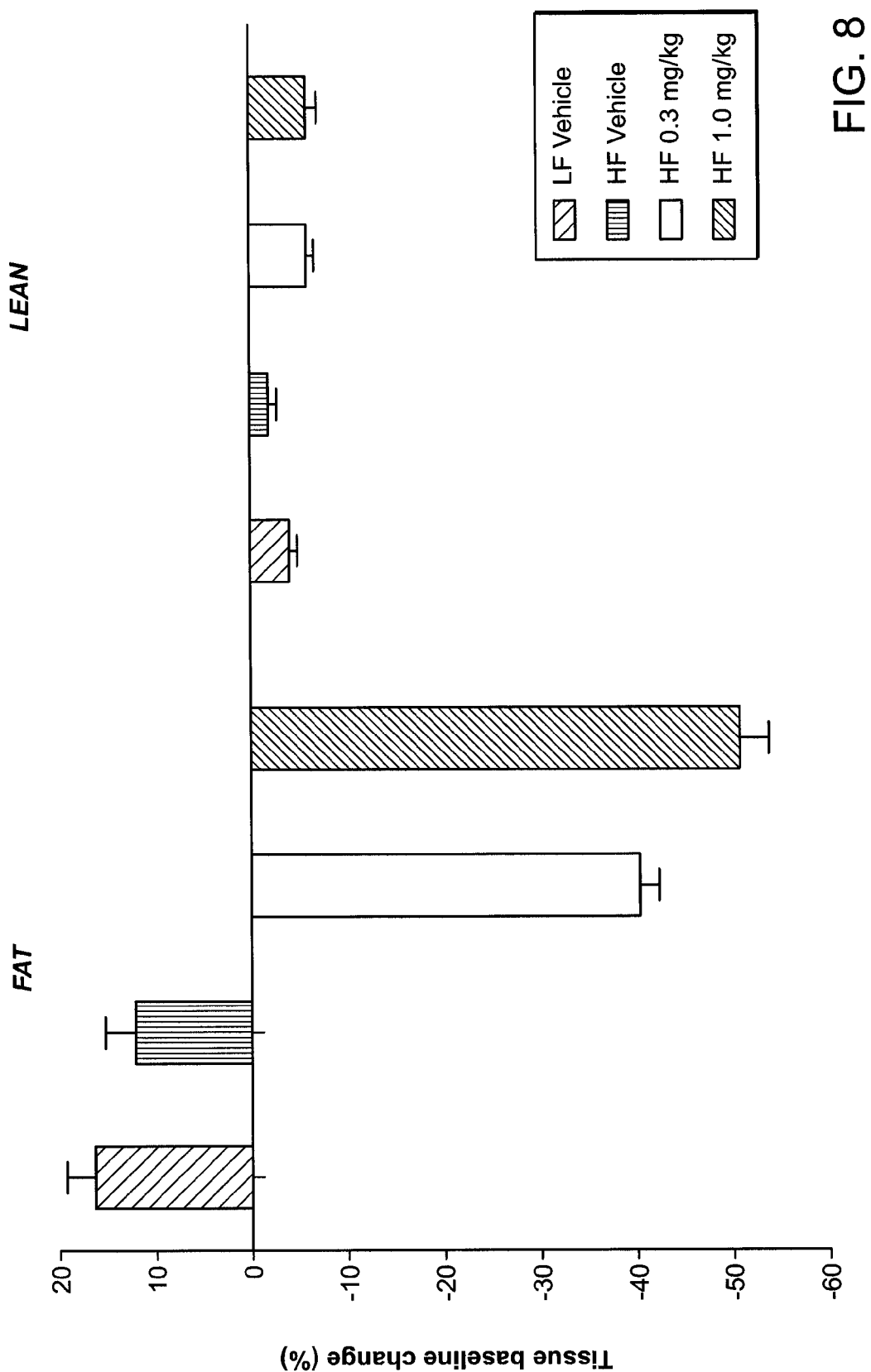
FIG. 8 is a bar graph showing percent fat change and lean mass changed resulting from administration of fumagillin at different dosages, as determined by NMR.
Figure 9:
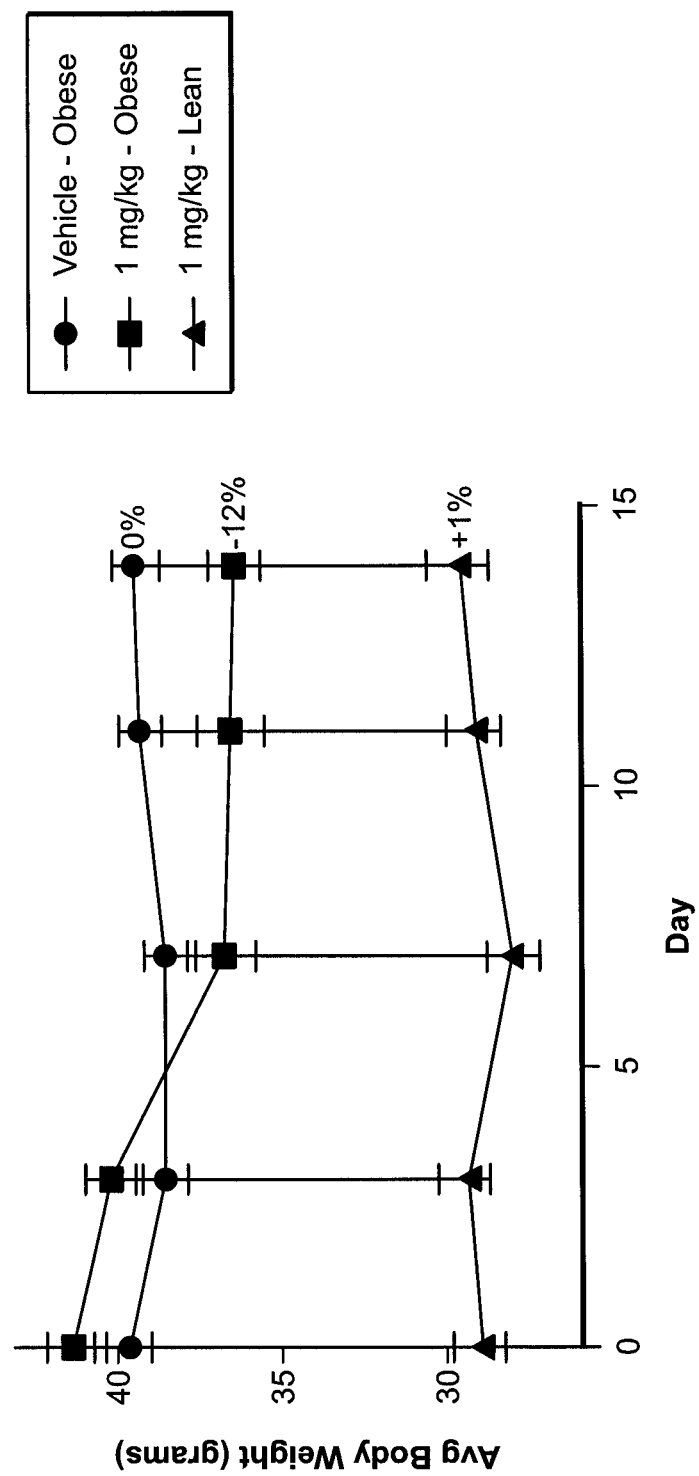
FIG. 9 is a line graph showing effects of fumagillin on obese mice and lean mice. Data is expressed as average body weight in grams.

The diet-induced obese group was further divided into three groups, one group administered fumagillin by oral gavage as a solution in 1% DMSO, at dose of 0.3 mg/kg/day, for 28 days, and the other group administered fumagillin by oral gavage as a solution in 1% DMSO, at dose of 1.0 mg/kg/day, for 28 days and the other administered 0.25% DMSO vehicle alone for 28 days. The lean group was administered 1% DMSO vehicle for 28 days. Percent fat change and percent lean mass change from baseline were determined by NMR after 28 days. Data herein demonstrate administering fumagillin at dosages that resulted in weight loss without resulting in substantial loss of lean body mass (FIGS. 8 and 9). Data show that diet-induced obese mice, administered either 0.3 mg/kg/day or 1.0 mg/kg/day lost significant amounts of weight over the 28 days, with the diet-induced obese mice administered 1.0 mg/kg/day losing a greater amount of weight (FIGS. 8 and 9).

Thus, data herein show that the present invention takes advantage of the potency and efficacy of fumagillin while overcoming harmful side-effects associated with the compound by administering fumagillin at dosages that do not substantially reduce lean body mass, therefore avoiding adverse side-effects such as wasting.

Example 7

Fumagillin is Poorly Absorbed Upon Oral Administration in a Capsule

A study was undertaken to investigate absorption of fumagillin orally administered in a capsule. Five male Sprague-Dawley rats were fasted, and were then each orally administered a non-enterically coated capsule containing 30 mg/kg of fumagillin. To determine absorption of fumagillin from the stomach, blood was collected from the jugular vein of each rat at time points of 0 min., 10 min. (graphically illustrated as 0.17), 20 min. (graphically illustrated as 0.33), 30 min. (graphically illustrated as 0.5), 2 hrs. and 8 hrs. Table 1 below shows results of oral administration of fumagillin in a capsule.

TABLE 1

Results of oral administration of fumagillin in a capsule

| 30 mg/kg capsule | ZGN-201 Conc. (ng/mL) in Rat Plasma | | | | | | |
|---|---|---|---|---|---|---|---|
| | Male | | | | | | |
| Time Point (hr) | 1 | 2 | 3 | 4 | 5 | Mean | STDEV |
| 0 | BQL | BQL | BQL | BQL | BQL | NA | NA |
| 0.17 | BQL | BQL | BQL | BQL | BQL | NA | NA |
| 0.33 | 5.3 | 1.9 | 1.6 | 1.8 | 5.2 | 3 | 2 |
| 0.5 | 14.3 | 4.5 | 3.6 | 3 | 11.4 | 7 | 5 |
| 1 | 36.1 | 14.5 | 8.9 | 3.6 | 117.9 | 36 | 47 |
| 2 | 81.2 | 98.2 | 125.4 | 9.5 | 156.4 | 94 | 55 |
| 8 | 36.6 | 47.1 | 141.3 | 31.6 | 116.8 | 75 | 51 |

Figure 10:
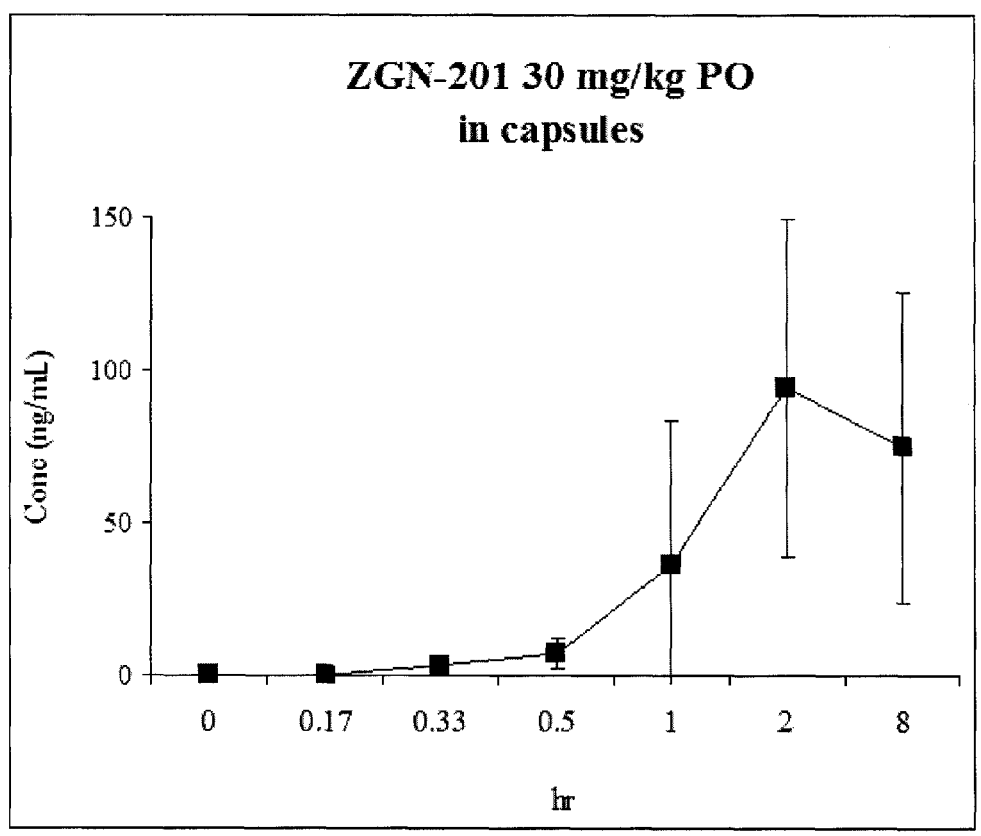
FIG. 10 is a line graph showing an absorption profile of fumagillin orally administered in a capsule over an eight hour period of time. Data is expressed as concentration (mg/ml) of fumagillin.

FIG. 10 graphically illustrates the results shown in Table 1. Data show that absorption of fumagillin through the stomach is not observed until 20 min. after the capsule is administered, with absorption peaking at approximately 2 hrs after administration of the capsule (Table 1 and FIG. 10, time points 0.33 and 2 respectively). Data further show that the maximal concentration of fumagillin absorbed through the stomach and into the blood was approximately 100 ng/ml (Table 1 and FIG. 10, time point 2). Data herein demonstrate that fumagillin presented a very small absorption profile and is poorly absorbed through the stomach.

A study was next designed to analyze an absorption profile of fumagillin with respect to the small intestine.

Example 8

Fumagillin Presents a Large Absorption Profile in the Small Intestine

A study was undertaken to investigate absorption of fumagillin from the small intestine. Five male Sprague-Dawley rats were fasted, and were then catheterized into the duodenum, 1.5 centimeters below the stomach. The stomachs of these rats were tied off so administration would bypass the stomach of each rat. Rats were then infused with 30 mg/kg of fumagillin and an equal volume of Trypan blue (Invitrogen). To determine absorption of fumagillin into the small intestine, blood was collected from the jugular vein of each rat at time points of 0 min., 5 min. (graphically illustrated as 0.083), 15 min. (graphically illustrated as 0.25), 30 min. (graphically illustrated as 0.5), 2 hrs, and 8 hrs. Table 2 below shows results of intraduodenal administration of fumagillin.

TABLE 2

Results of intraduodenal administration of fumagillin

| 30 mg/kg Intestinal Administration | Fumagillin Conc. (ng/mL) in Rat Plasma | | | | | |
|---|---|---|---|---|---|---|
| | Male | | | | | |
| Time Point (hr) | 1 | 3 | 4 | 5 | Mean | STDEV |
| 0 | 1 | BQL | BQL | BQL | NA | NA |
| 0.083 | 31433.4 | 30286.5 | 30532.1 | 31057 | 25093 | 12829 |
| 0.25 | 7705.8 | 9275.7 | 9903.7 | 13584.2 | 9204 | 2969 |
| 0.5 | 1104.6 | 2295 | 1109.8 | 1225.1 | 1732 | 833 |
| 2 | 95 | 66.5 | 79.3 | 27.5 | 506 | 983 |
| 8 | 11.9 | 9 | 6.9 | 6.8 | 20 | 26 |

BQL: 1 ng/mL

Figure 11:
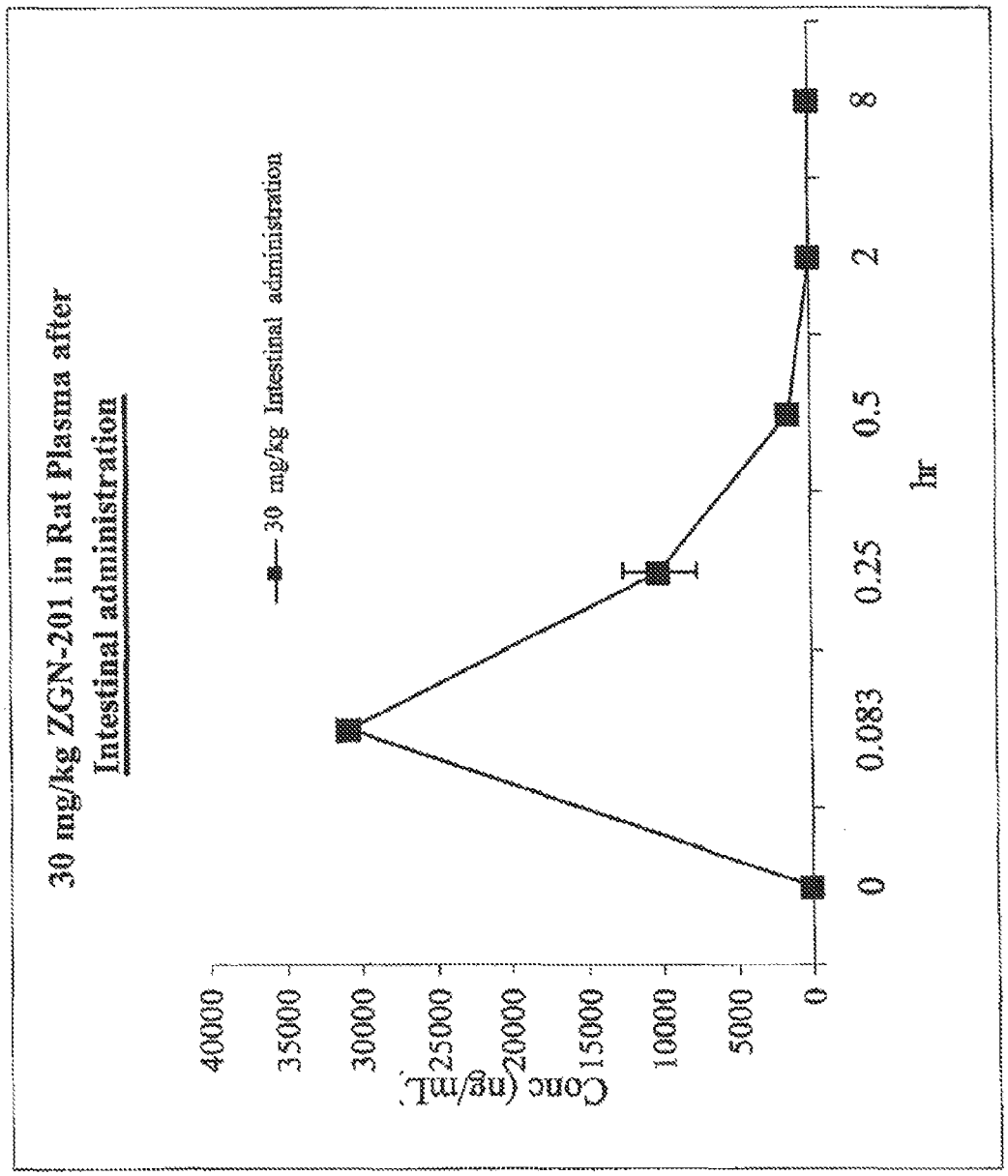
FIG. 11 is a line graph showing an absorption profile of fumagillin in a small intestine of a rat over an eight hour period of time. Data is expressed as concentration (mg/ml) of fumagillin.

FIG. 11 graphically illustrates the results shown in Table 2. Data show a large amount of absorption of fumagillin (3000 ng/ml) by the small intestine as early as 5 min. from administration of the compound (Table 2 and FIG. 11, time point 0.083). By 30 min. after administration of fumagillin, there was only a small amount of the compound still being absorbed by the small intestine of the rats (Table 2 and FIG. 11, time point 0.50). Data herein demonstrate that fumagillin presented a large absorption profile in the small intestine compared to the absorption profile of fumagillin through the stomach.

A study was next designed to further analyze affect of fumagillin on different types of blood cells.

Example 9

Administering Fumagillin Dosages that Do Not Result in Blood Disorders

Blood disorders, e.g., thrombocytopenia, leukopenia, and neutropenia, are undesirable side-effects of administration of a drug. A study was undertaken to analyze effects of fumagillin on different types of blood cells.

Male lean Sprague-Dawley rats were divided into two groups, ten rats per group. One group of rats received fumagillin by oral gavage as a solution in 10% DMSO, at dose of 3 mg/kg. Administration of fumagillin to this group of rats was performed on day 3 and day 9 of the study. The other group of rats was administered by oral gavage a solution of 10% DMSO/90% water (vehicle-only). Administration of vehicle to this group of rats was performed on day 3 and day 9 of the study. Blood samples were collected daily for complete blood analysis (CBC).

Figure 12:
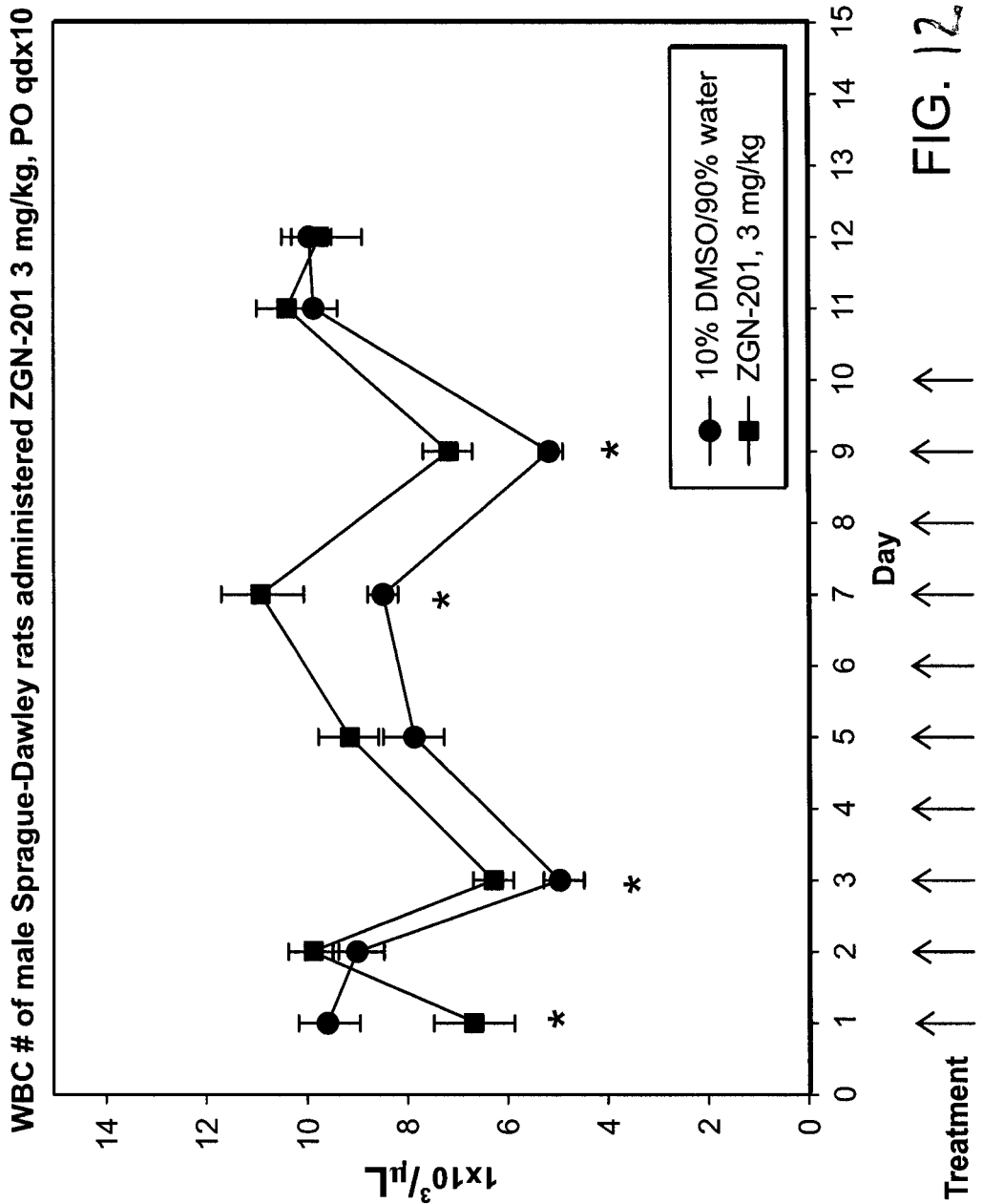
FIG. 12 is a line graph showing effects of fumagillin on white blood cell count in rats. Data is expressed as white blood cells/µL.

Data show the white blood cell count of fumagillin administered rats on day 3 was approximately 5000 white blood cells/µL, compared to the white blood cell count of vehicle-only rats on day 3, which was observed to be approximately 6100 white blood cells/µL (FIG. 12). Data further show the white blood cell count of fumagillin administered rats on day 9 was approximately 5200 white blood cells/µL, compared to the white blood cell count of vehicle-only rats on day 9, which was observed to be approximately 7000 white blood cells/µL (FIG. 12).

Figure 13:
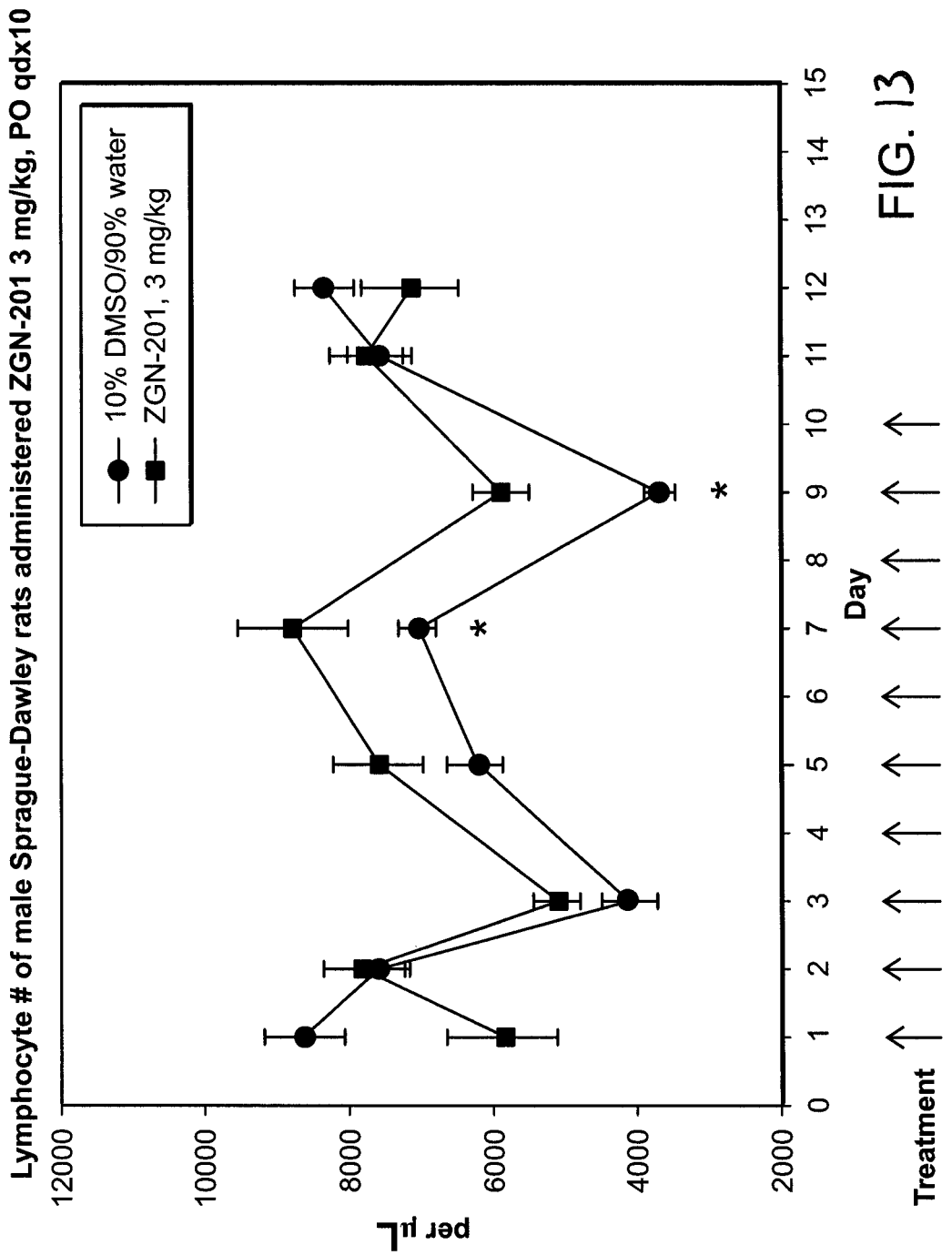
FIG. 13 is a line graph showing effects of fumagillin on lymphocyte count in rats. Data is expressed as lymphocytes/µL.

Lymphocyte count of fumagillin administered rats on day 3 was approximately 4000 lymphocytes/µL, compared to the lymphocyte count of vehicle-only rats on day 3, which was observed to be approximately 5000 lymphocytes/µL (FIG. 13). The lymphocyte count of fumagillin administered rats on day 9 was approximately 3900 lymphocytes/µL, compared to the lymphocyte count of vehicle-only rats on day 9, which was observed to be approximately 6000 lymphocytes/µL (FIG. 13).

Figure 14:
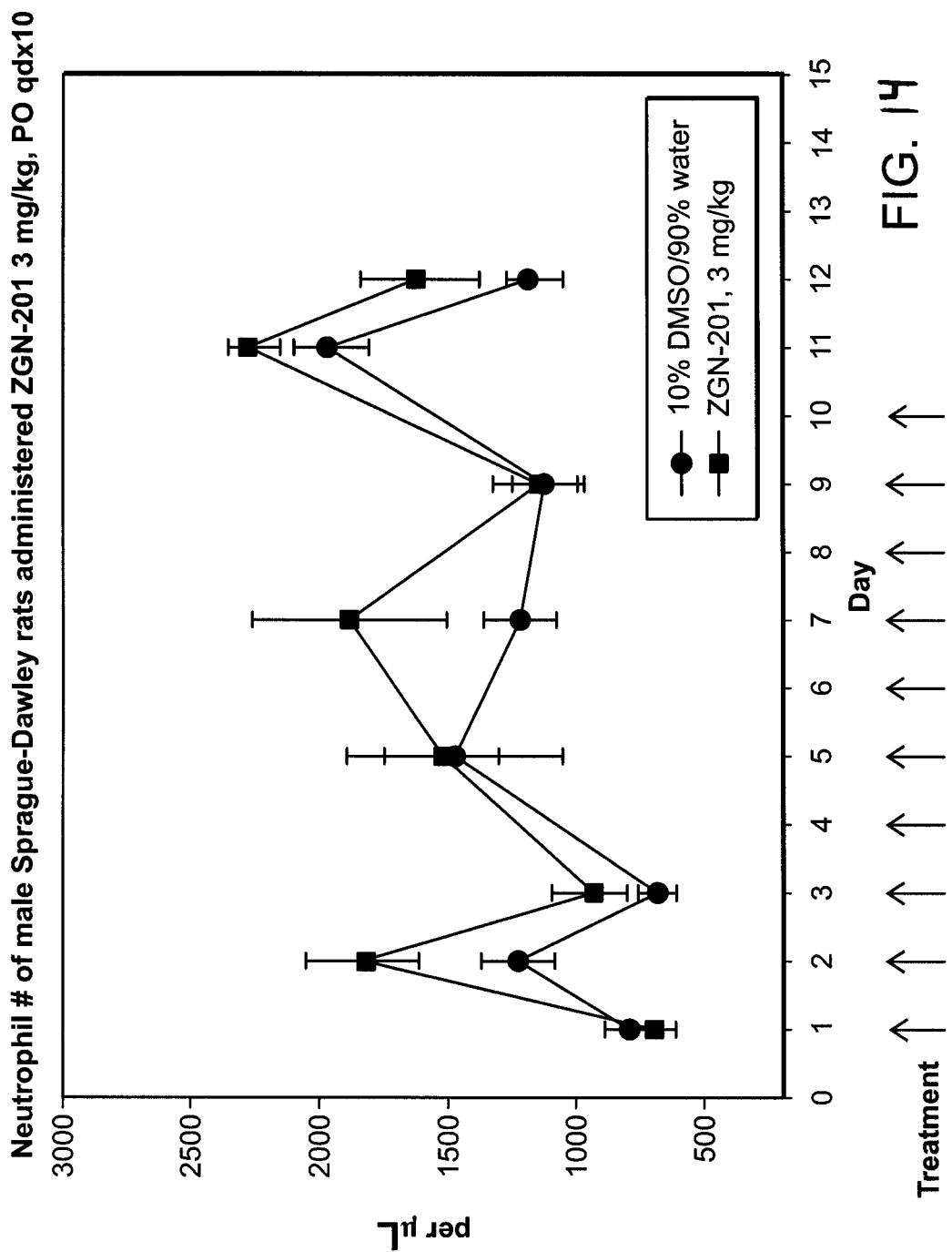
FIG. 14 is a line graph showing effects of fumagillin on neutrophil count in rats. Data is expressed as neutrophils/µL.

Neutrophil count of fumagillin administered rats on day 3 was approximately 650 neutrophils/µL, compared to the neutrophil count of vehicle-only rats on day 3, which was observed to be approximately 1200 neutrophils/µL (FIG. 14). Data further show that the neutrophil count of fumagillin administered rats on day 9 was approximately 1100 neutrophils/µL, compared to the neutrophil count of vehicle-only rats on day 9, which was observed to be approximately 1100 neutrophils/µL (FIG. 14).

A portion of the decline in each of white blood cell count, lymphocyte count, and neutrophil count on day 3 was attributed to stress related to dosing and blood collection.

Statistical analysis of the data for each of white blood cell count, lymphocyte count, and neutrophil count, revealed that the variation between fumagillin administered rats and vehicle-only administered rats for each of white blood cell count, lymphocyte count, and neutrophil count was not statistically significant. Therefore, the above data demonstrate administering fumagillin at dosages that do not result in development of a blood disorder. In fact, administering fumagillin in amounts greater than 9 mg/kg/day does not result in development of a blood disorder.

Example 10

Effect of Fumagillin on Plasma Markers

The hormone leptin, produced by adipocytes, is thought to act as a lipostat, i.e., as the amount of fat stored in adipocytes rises, leptin is released into the blood and signals to the brain that the body has enough to eat. However, most overweight people have high levels of leptin in their bloodstream. A study was designed to analyze effects of fumagillin on leptin.

Mice were divided into four groups, a diet-induced obese group administered fumagillin at 1 mg/kg/day (oral gavage as a solution in 0.25% DMSO), a Pair-fed group, a caloric restriction group, and a diet-induced obese group. For the diet-induced obese groups, C57BL/6 mice were maintained prior to and during the study on a diet containing 42% fat on a kilocalorie basis. Plasma markers were measured prior to and at the end of the study.

Figure 15:
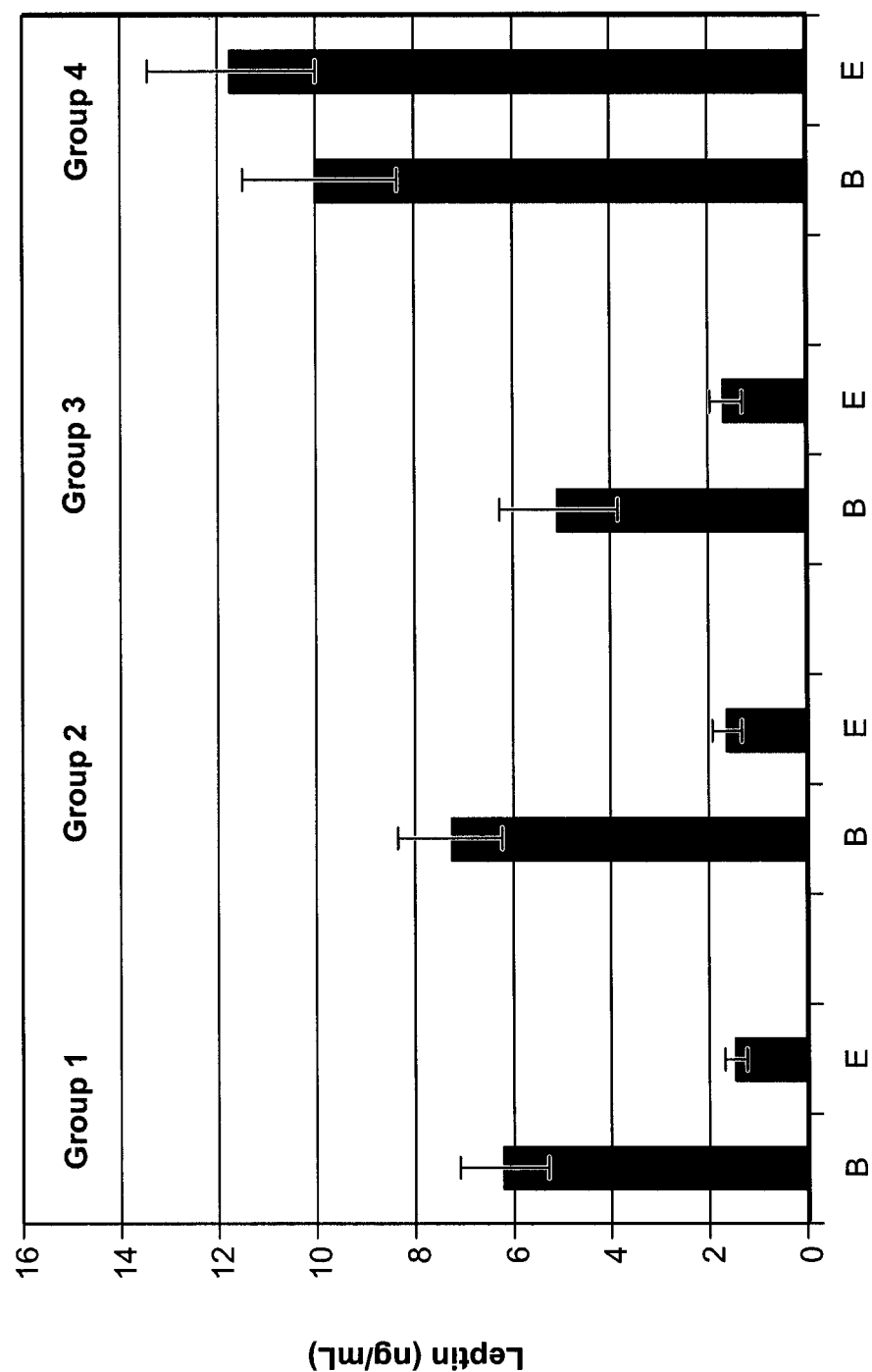
FIG. 15 is a bar graph showing effects of fumagillin on leptin levels. Data is expressed as mg/ml of leptin.

Data show that leptin levels were reduced in the diet-induced obese group administered fumagillin (FIG. 15). Similarly, leptin levels decreased in the Pair-fed and caloric restriction group (FIG. 15). The leptin level at the end of the study of diet-induced obese mice administered fumagillin was similar to the leptin level in each of the pair fed group and the caloric restriction group (FIG. 15). In contrast, the diet-induced obese group not administered fumagillin had significantly increased leptin levels by the end of the study (FIG. 15).

Example 11

Oral Cavity Administration of Fumagillin

Fumagillin has been limited by poor bioavailability of the molecule, i.e., fumagillin exhibits rapid metabolic degradation due to absorption in the gastrointestinal tract and erratic levels in blood. A study is designed to investigate oral cavity pharmaceutical formulations including fumagillin, in particular formulations for buccal and sublingual administration.

A buccal tablet, a sublingual tablet, and an ointment are prepared as follows. For the buccal and sublingual tablet, a mixture is prepared from fumagillin, fumagillol, or fumagillin ketone, or derivatives thereof, or salts, esters or prodrugs of these, anhydrous lactose, and magnesium stearate. Using a flat face punch, 6 mm in diameter, the mixture is compressed into tablets, each having a weight of 90 mg and a hardness (Erweka hardness tester) of 3 kg. The ointment is prepared by kneading fumagillin, fumagillol, or fumagillin ketone, or derivatives thereof, or salts, esters or prodrugs of these, with white petrolatum.

Obesity is induced by a high-fat diet in mice. Twelve week-old C57BL/6NTac mice, are maintained on a 60% fat diet prior to and during the study, and are separated into five groups, eight animals per group. The first group of mice is administered daily the buccal tablet of fumagillin, the second group of mice is administered daily the sublingual tablet of fumagillin, the third group of mice is administered daily the ointment of fumagillin, the fourth group of mice is administered daily fumagillin by oral gavage as a solution in 10% DMSO (control), and the fifth group is administered daily a 10% DMSO solution by oral gavage (vehicle-only). Weight of mice is measured for 30 days.

Data is expected to show that fumagillin that is administered in each of the buccal tablet, the sublingual tablet, and the ointment to diet-induced obese mice is effective for providing weight loss. Weight loss is observed by the end of the study for groups receiving each of the oral cavity formulations including fumagillin, as a percentage of pre-study weight. Data is also expected to show that weight loss is observed in control diet-induced obese mice by the end of the study, as a percentage of pre-study weight. In contrast, vehicle-only mice show a non-significant weight loss.

Less weight loss is observed in control diet-induced obese mice compared to weight loss that is observed in each group of mice receiving each of the oral cavity formulations, i.e., the buccal tablet, the sublingual tablet, and the ointment. The above data will demonstrate that buccal and sublingual administration of fumagillin appears to be more efficacious than oral administration of fumagillin. Thus the formulations of the invention improve the bioavailability of fumagillin to take advantage of the efficacy of the molecule for weight reduction.

What is claimed is:

1. A method of treating an overweight or obese subject, the method comprising: orally administering to the subject in need thereof, about 0.001 mg/kg to about 1 mg/kg of body weight per day of fumagillin, or fumagillol, or salts or esters thereof, effective to result in weight loss in the subject.

2. The method according to claim 1, wherein the amount of fumagillin or fumagillol administered to the subject is about 0.1 mg/kg/day or lower.

3. The method according to claim 1, wherein the subject is a human.

4. The method according to claim 1, wherein the subject is a cat or a dog.

5. The method according to claim 3, wherein the subject has a Body Mass Index of at least about 25 $kg/m^2$.

6. The method according to claim 3, wherein the subject has a BMI of at least about 35 $kg/m^2$ and an overweight- or obesity-related condition.

7. The method of claim 1, further comprising administering a weight loss agent to said subject.

8. The method of claim 2, wherein the amount of fumagillin or fumagillol administered to the subject is about 0.01 mg/kg/day.

9. A method of treating an overweight or obese cat or dog in need thereof, the method comprising orally administering about 0.001 mg to about 1 mg of fumagillol per kg of body weight of the cat or dog per day to the overweight cat or dog.

* * * * *